US007914451B2

(12) United States Patent
Davies

(10) Patent No.: US 7,914,451 B2
(45) Date of Patent: Mar. 29, 2011

(54) DETERMINING ATTRIBUTES USING ULTRASOUND

(75) Inventor: Tim Davies, Calgary (CA)

(73) Assignee: InnerVision Medical Technologies Inc., Calgary (CA)

( * ) Notice: Subject to any disclaimer, the term of this patent is extended or adjusted under 35 U.S.C. 154(b) by 753 days.

(21) Appl. No.: 11/226,957

(22) Filed: Sep. 15, 2005

(65) Prior Publication Data

US 2007/0060817 A1 Mar. 15, 2007

(51) Int. Cl.
*A61B 8/00* (2006.01)
(52) U.S. Cl. .......................... 600/437; 382/128
(58) Field of Classification Search ............... 600/437, 600/438, 442, 448; 382/128; 367/87; 181/101; 73/579, 597, 602
See application file for complete search history.

(56) References Cited

U.S. PATENT DOCUMENTS

| | | | |
|---|---|---|---|
| 4,072,922 A | 2/1978 | Taner et al. | |
| 4,105,018 A * | 8/1978 | Greenleaf et al. | 73/597 |
| 4,259,733 A | 3/1981 | Taner et al. | |
| 4,539,847 A * | 9/1985 | Paap | 73/579 |
| 4,662,222 A * | 5/1987 | Johnson | 73/602 |
| 5,141,738 A | 8/1992 | Rasor et al. | |
| 5,197,475 A | 3/1993 | Antich et al. | |
| 5,226,019 A | 7/1993 | Bahorich | |
| 5,293,871 A * | 3/1994 | Reinstein et al. | 600/442 |
| 5,673,697 A | 10/1997 | Bryan et al. | |
| 5,720,291 A | 2/1998 | Schwartz | |
| 5,784,334 A | 7/1998 | Sena et al. | |
| 5,785,654 A | 7/1998 | Iinuma et al. | |
| 5,838,564 A | 11/1998 | Bahorich et al. | |
| 5,850,622 A | 12/1998 | Vassiliou et al. | |
| 5,862,100 A | 1/1999 | VerWest | |
| 5,870,691 A | 2/1999 | Partyka et al. | |
| 5,892,732 A | 4/1999 | Gersztenkorn | |
| 5,920,285 A | 7/1999 | Benjamin | |
| 5,930,730 A | 7/1999 | Marfurt et al. | |

(Continued)

FOREIGN PATENT DOCUMENTS

WO 9312444 A2 6/1993

(Continued)

OTHER PUBLICATIONS

R. C. Uden, et al. "Neural Network Training For Reservoir Characterizations of Litho Facies", *Rock Solid Images EAGE 65th Conference & Exhibition*, Jun. 2003.

(Continued)

*Primary Examiner* — Eric F Winakur
*Assistant Examiner* — Vani Gupta
(74) *Attorney, Agent, or Firm* — Oyen Wiggs Green & Mutala LLP

(57) ABSTRACT

Systems and methods are described for determining tissue attributes using ultrasound energy. Various characteristics of a medium, such as an animal tissue, can be estimated using techniques such as signal trace analysis and angular-dependency analysis of reflectivity. Such techniques can be performed in conjunction with a spectral decomposition analysis. Attributes can be cross-plotted so as to facilitate user analysis and better understanding of the medium. Attributes obtained in the foregoing manner do not necessarily need to conform to standard values, especially when attempting to detect and characterize an anomaly within the medium. Relative differences of attribute values within the medium can provide information about the anomaly. Additional information about the anomaly can be provided by an observation of the anomaly by an expert.

80 Claims, 18 Drawing Sheets

U.S. PATENT DOCUMENTS

| | | | |
|---|---|---|---|
| 5,940,778 | A | 8/1999 | Marfurt et al. |
| 5,969,661 | A | 10/1999 | Benjamin |
| 6,058,074 | A | 5/2000 | Swan et al. |
| 6,092,026 | A | 7/2000 | Bahorich et al. |
| 6,135,960 | A | 10/2000 | Holmberg |
| 6,138,075 | A | 10/2000 | Yost |
| 6,213,958 | B1 | 4/2001 | Winder |
| 6,238,342 | B1 | 5/2001 | Feleppa et al. |
| 6,278,949 | B1 | 8/2001 | Alam |
| 6,289,230 | B1 | 9/2001 | Chaiken et al. |
| 6,374,185 | B1 | 4/2002 | Taner et al. |
| 6,475,150 | B2 | 11/2002 | Haddad |
| 6,480,790 | B1 | 11/2002 | Calvert et al. |
| 6,487,502 | B1 | 11/2002 | Taner |
| 6,499,536 | B1 | 12/2002 | Ellingsen |
| 6,585,647 | B1 | 7/2003 | Winder |
| 6,668,654 | B2 | 12/2003 | Dubois et al. |
| 6,681,185 | B1 | 1/2004 | Young et al. |
| 6,755,787 | B2 | 6/2004 | Hossack et al. |
| 6,847,737 | B1 | 1/2005 | Kouri et al. |
| 7,283,652 | B2 * | 10/2007 | Mendonca et al. .......... 382/128 |
| 2004/0236217 | A1 | 11/2004 | Cerwin et al. |
| 2005/0215883 | A1 * | 9/2005 | Hundley et al. ............... 600/410 |

FOREIGN PATENT DOCUMENTS

WO               0043809 A1     7/2000

OTHER PUBLICATIONS

Albert E. Brown. "Rationale And Summary Of Methods For Determining Ultrasonic Properties Of Materials At Lawrence Livermore National Laboratory." *Lawrence Livermore National Laboratory*, Apr. 25, 1997.
"Geophysical Ground Stiffness Determination", *Technical Summary Sheet No. 10*.
"Biomedical Imaging And Emerging Technologies: Practical Manual", *School Of Biophysical Sciences And Electrical Engineering*, 2003 Edition.
Oleg Michailovich, et al. "Phase Unwrapping For 2-D Blind Deconvolution Of Ultrasound Images", *IEEE Transactions On Medical Imaging*, vol. 23, No. 1, pp. 7-25, Jan. 2004.
Karl Marfurt et al. "Comparison Of 3-D Edge Detection Seismic Attributes To Vinton Dome Louisiana".
Cynthia Bruynes and Mark Ottensmeyer. "Measurements Of Soft-Tissue Mechanical Properties To Support Development Of A Physically Based Virtual Animal Model." *BioVis Technology Center*, et al.
Mike Bahorich, et al. "Amplitude Responses Image Reservoir", *Hart's E & P*, p. 59-61, Jan. 2002.
"Seismic Trace Attributes And Their Projected Use In Prediction Of Rock Properties And Seismic Facies", *Rock Solid Images*, pp. 1-4.
Greg A. Partyka. "Seismic Attribute Sensitivity To Energy, Bandwidth, Phase And Thickness", *BPAmoco*.
"EMERGE Theory", *EMERGE*, Jul. 1988.
Greg Partyka, et al. "Interpretational Applications Of Spectral Decomposition", Amoco Production Company, *Leading Edge*, vol. 18, No. 3, pp. 353-360, 1999.
Z. Fang, et al. "Comptuer-Aided Characterization For Effective Mechanical Properties Of Porous Tissue Scaffolds", *Department of Mechanical Engineering, Drexel University, Elsevier Ltd.* 2004.
Dr. M. Turhan (Tury) Taner, "Kohonen's Self Organizing Networks with 'Conscience'", *Rock Solid Images*, Nov. 1997.
M. Alper Kutay, et al. "Breast Tissue Characterization Based On Modeling Of Ultrasonic Echoes Using The Power-Law Shot Noise Model", *Elsevier Preprint*, Aug. 17, 2001.
Per Avseth, et al. "Diagnosing High-Porosity Sands For Reservoir Characterization Using Sonic And Seismic", *Stanford University and Norsk Hydro USA*.
"Seismic Fracture Detection: Exploiting The Range Of Seismic Signatures Using Rock Physics Priciples" *Rock Solid Images* (www.rocksolidimages.com).
Robert G. Clapp, et al. "Iterative Resolution Estimation In Kirchhoff Imaging", *Stanford Exploration Project , Report 102*, Oct. 25, 1999, pp. 35-46.
Greg Partyka, et al. "Interpretational Applications Of Spectral Decomposition In Reservoir Characterization" , *The Leading Edge*, Mar. 1999, pp. 353-360.
Elizabeth Lorenzetti Harvey, et al. "Techniques For Volume Interpretation Of Seismic Attributes." *Expanded Abstracts*, 2000.
John J. Zhang, et al. "Complex Seismic Trace Analysis And Its Applications to Time-Lapse Seismic Surveys", *CREWES, Geology and Geophysics, University of Calgary*.
E. R. (Ross) Crain, P. Eng. "The New Role Of Petrophysics In Geophysical Interpretation.", CSEG Recorder, Sep. 2003.
Frederic Noo, et al. "A Two-Step Hilbert Transform Method For 2D Image Reconstruction", *IOP Publishing Ltd*, 2004.
Stewart A. Levin, "Reducing Uncertainty With Seismic Attributes: Examples And Challenges" *Landmark Graphics Corporation*.
"Table 1: Seismic Attributes Categories And Analysis Methods", *Explorer*, Jan. 2005 (web article).
Maya Ekibbi, et al. "The Geysers Geothermal Field II: Modeling Crack-Induced Anisotropy In The Subsurface", *Department of Geological Science, University of North Carolina at Chapel Hill*.
Yi Luo, et al. "Generalized Hilbert Transform And Its Applications In Geophysics", *The Leading Edge*, V. 22, No. 3, pp. 198-202, Mar. 2003.
"Seismic Analysis", *Web Article*, Jan. 2006.
R. L. C. Van Spaendonck, et al. "Local Hilbert Transformation For Seismic Attributes", *EAGE 64th Conference & Technology Exhibition*, May 27-30, 2002.
Guillaume Cambios. "Can P-Wave AVO Be Quantitative?" *The Leading Edge*, V. 19, No. 11, pp. 1246-1251, Nov. 2000.
B. P. Bonner, et al. "Ultrasonic Characterization Of Synthetic Soils For Application To Near Surface Geophysics." *Presented at SAGEEP Meeting*, 1999, etc.
Ali Y. Sayed. "In Situ Compressional Wave Velocity Across An Exposed Brittle Fault Zone", Copyright Ali Y. Sayed, 2001.
Arnim B. Haase, "Approximation Errors In AVO-Analysis And Inversion", *Geo-X Systems, Ltd*.
Yexin Liu, et al. "Mapping Rock Mechanical Properties With Seismic Attribute-Based Support Vector Machine (SVM) Technique", *Department of Physics, Institute For Geophysical Research, University of Alberta, Edmonton*.
Arthur E. Barnes, "Seismic Attributes In Your Facies", *CSEG Recorder*, Sep. 2001.
Guillaume Cambois. "AVO Processing: Myths And Reality", *CSEG Recorder*, Mar. 2001.
Michael Burianyk, et al. "Amplitude-Vs-Offset And Seismic Rock Property Analysis: A Primer", *CSEG Recorder*, Nov. 2000.
John J. Zhang et al. "Complex Seismic Trace Analysis And Its Application To Time-Laps Seismic Surveys", *CREWS, Geology And Geophysics, University of Calgary*.
Tracy J. Stark. "Unwrapping Instantaneous Phase To Generate A Relative Geologic Time Volume", *SEG Expanded Abstract* , 2003.
Ivan Magrin-Chagnolleau, et al. "Empirical Mode Decomposition Based Time-Frequency Attributes", *Rice University*.
M. Turhan Taner, "Attributes Revisited" *Rock Solid Images*, 1992 (Revised Sep. 2000).
Richard L. Chambers, et al. "Quantitative Use Of Seismic Attributes For Reservoir Characterization", *Quantative Geoscience, Inc*.
Brian H. Russell, et al. "The AVO Modelling Volume".
"Announcements", *The Leading Edge*, pp. 445-446, Apr. 2001.
Martin Ester, et al. "Knowledge Discovery In Spatial Databases", Invited Paper at 23rd *German Confer. On Artificial Intelligence (KI '99)*, Bonn, Germany, 1999.
Amin, et al., "Application of Neural Network to Ultrasound Tissue Characterization Using Backscattered Signal Parameters," Oct. 25-31, 1992, pp. 1357-1359, vol. 2, Nuclear Science Symposium and Medical imaging Conference, 1992, Conference Record of the 1992 IEEE.
International Search Report for PCT/IB2005/003674, filed Sep. 16, 2005.

* cited by examiner

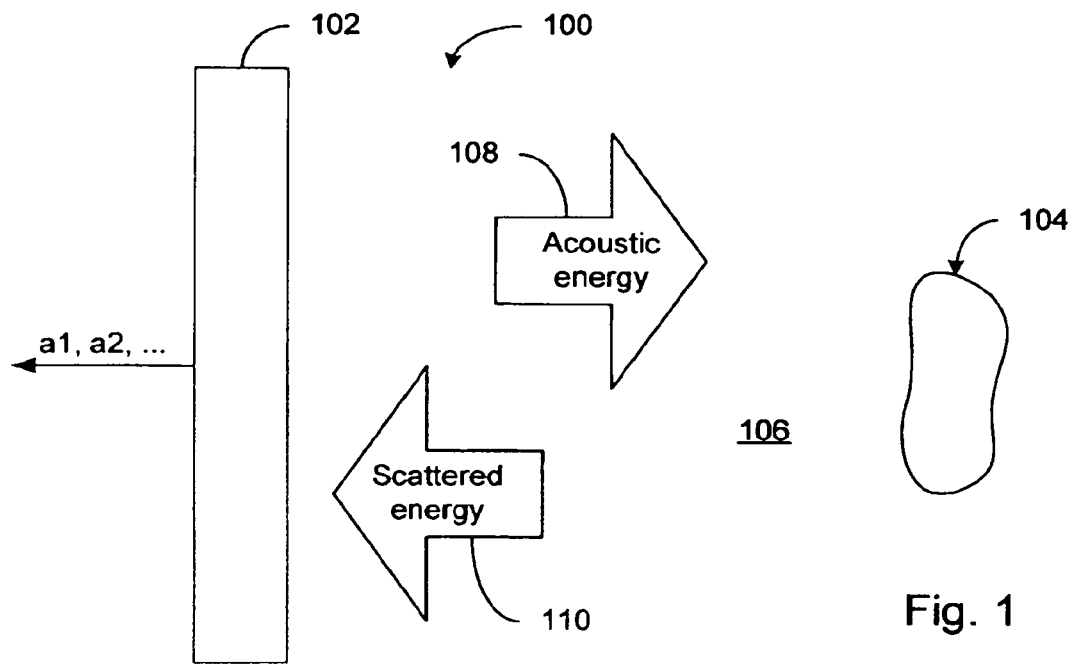
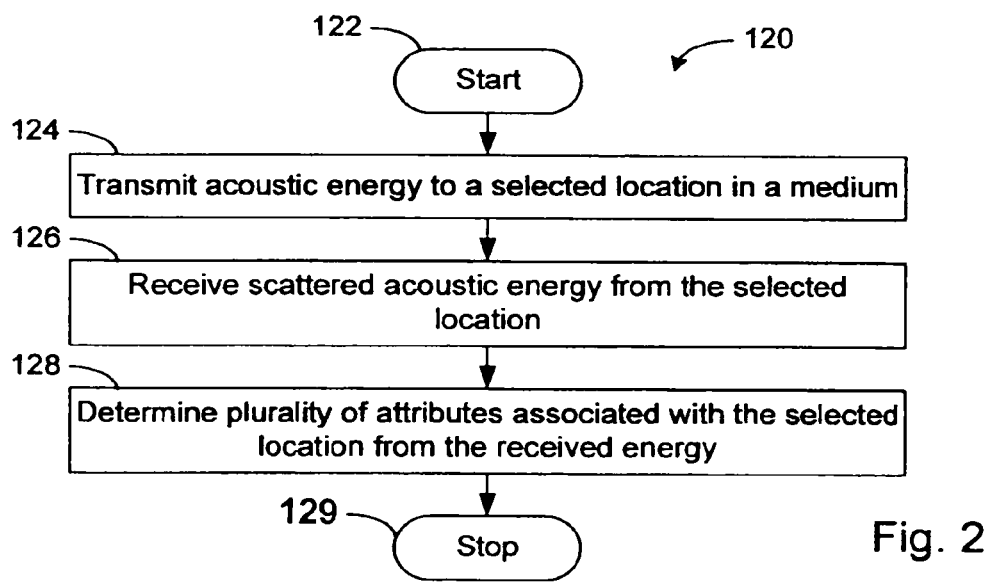

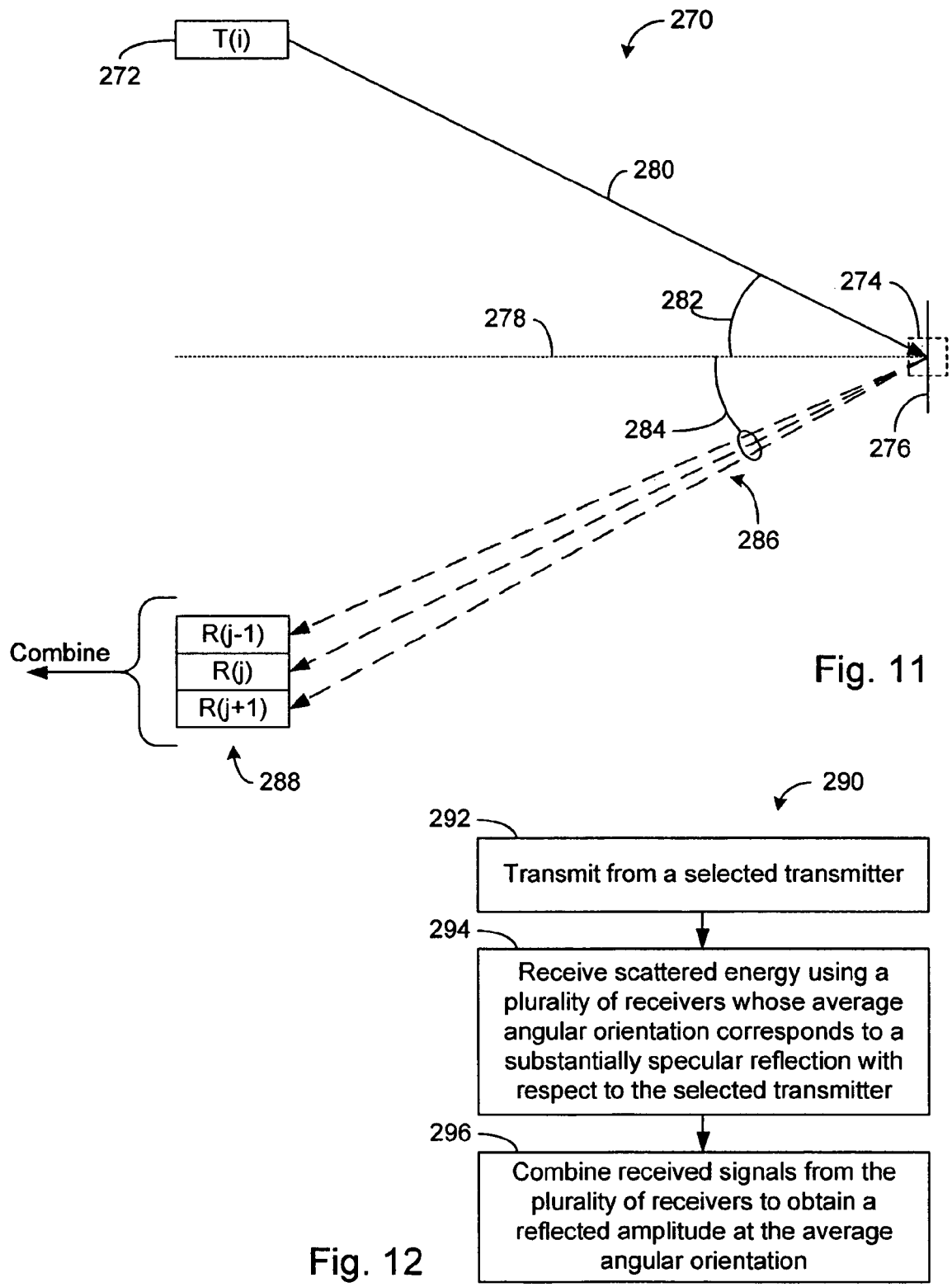

DETERMINING ATTRIBUTES USING ULTRASOUND

BACKGROUND

1. Field

The present teachings generally relate to ultrasound technology and, in particular, to systems and methods for determining attributes of an object based on its interaction with acoustic energy.

2. Description of the Related Art

In conventional ultrasound devices, an image of a reflecting object in a medium is formed by analyzing the propagation time and amplitude of the reflected acoustic energy. Such devices are typically configured so as to optimize some combination of resolution, ease of use, and other imaging-related performance parameters.

Thus, conventional ultrasound devices can detect an object in the medium based on visual contrast between the object and the surrounding medium. Such differences in contrast generally result from differences in reflecting properties of the medium and the object. Even if the object is detected in the foregoing manner, information about the object is usually limited to the visual interpretation of the contrast image.

SUMMARY

The present teachings generally relate to a system and method for determining attributes using ultrasound energy. Various characteristics of a medium such as an animal tissue can be estimated using techniques such as signal trace analysis and angular-dependency analysis of reflectivity. Such techniques can be performed in conjunction with a spectral decomposition analysis. Attributes can be cross-plotted so as to facilitate user analysis and better understanding of the medium. Attributes obtained in the foregoing manner do not necessarily need to conform to some standard values, especially when attempting to detect and characterize an anomaly within the medium. Relative differences of the attribute values within the medium can provide information about the anomaly. Additional information about the anomaly can be provided by an observation of the anomaly by an expert.

One embodiment of the present teachings relates to a method for determining an attribute of an animal tissue using acoustic energy. The method includes receiving acoustic energy that has been reflected from the animal tissue. The method further includes generating an electrical signal from the received acoustic energy. The method further includes processing the electrical signal so as to generate a value of the attribute of the animal tissue, with the attribute being selected from the group consisting of an amplitude-variations-with-offset characteristic and a signal trace characteristic. The method further includes registering the value of the attribute in a computer storage.

In one embodiment, the tissue attribute includes the amplitude-variations-with-offset characteristic. In one embodiment, the tissue attribute includes the signal trace characteristic. In one embodiment, the tissue attribute further includes a spatial characteristic.

In one embodiment where the tissue attribute includes the amplitude-variations-with-offset characteristic, the amplitude-variations-with-offset characteristic includes a plot of a plurality of values corresponding to reflection amplitudes R of the received acoustic energy versus values corresponding to respective reflection angles $\theta$ of the reflection amplitudes, with the reflection angles $\theta$ being with respect to a layer in the animal tissue.

In one embodiment, the amplitude-variations-with-offset characteristic includes a functional relationship R estimated from an R versus $\theta$ plot.

In one embodiment, the functional relationship R includes a relationship $R(\theta)=A+B\sin^2\theta+C\sin^2\theta\tan^2\theta$ where parameters A, B, and C are constants that can be estimated from the R versus $\theta$ plot. In one embodiment, the method further includes estimating values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(4A-9B+5C)/8$ with an assumption that velocity $V_P$ of the compressional component is approximately three times that of velocity $V_S$ of the shear component in the animal tissue.

In another embodiment, the amplitude-variations-with-offset characteristic includes a functional relationship estimated from an R versus $\sin^2\theta$ plot. In one embodiment, the functional relationship R includes a relationship $R\theta=A+B\sin^2\theta$, where parameters A and B are estimated from the R versus $\sin^2\theta$ plot, with the A being representative of an intercept, and B being representative of a slope of a linear relationship estimated between R and $\sin^2\theta$. In one embodiment, the method further includes estimating values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(A-B)/2$ with an assumption that velocity $V_P$ of the compressional component is approximately twice that of velocity $V_S$ of the shear component in the animal tissue.

In one embodiment, the method further includes inverting reflectivity values $R_{P0}$ and $R_{S0}$ so as to obtain estimated values of impedance $Z_P$ and $Z_S$ respectively corresponding to compressional and shear components of the animal tissue. In one embodiment, the method further includes estimating one or more elastic properties of the animal tissue based on the estimated impedance values $Z_P$ and $Z_S$. In one embodiment, the one or more elastic properties include a rigidity parameter $\mu$ that corresponds to resistance to shear deformation, and estimated by a relationship $\mu=Z_S^2/\rho$, where $\rho$ represents an estimate of the density of the animal tissue. In one embodiment, the one or more elastic properties further include an elastic parameter $\lambda$ that is sensitive to fluid content of the animal tissue, with the elastic parameter $\lambda$ being estimated by a relationship $\lambda=(Z_P^2-2Z_S^2)/\rho$. In one embodiment, the one or more elastic properties further include a parameter $\kappa$ that corresponds to incompressibility or bulk modulus of the animal tissue, with the parameter $\kappa$ being estimated by a relationship $\kappa=\lambda+(2/3)\mu$.

In one embodiment where the tissue attribute includes the signal trace characteristic, the signal trace characteristic includes a complex function $F(t)=f(t)+ig(t)$, where $f(t)$ includes a real part of $F(t)$ and represents the electrical signal corresponding to a given region in the animal tissue, and $g(t)$ includes an imaginary part of $F(t)$ and represents a Hilbert transform of $f(t)$.

In one embodiment, the signal trace characteristic further includes a modulus $E(t)$ of the complex function $F(t)$ expressed as $E(t)=(f^2(t)+g^2(t))^{1/2}$. In one embodiment, the $E(t)$ represents an envelope of the electrical signal. In one embodiment, square of the $E(t)$ represents a value corresponding to a substantially instantaneous energy associated with the received acoustic energy. In one embodiment, the signal trace characteristic further includes a rate of change of the E(t) with respect to time, expressed as d(E(t))/dt. In one embodiment, the d(E(t))/dt provides information about absorption effects in the animal tissue. In one embodiment, the signal trace characteristic further includes a rate of change of the d(E(t))/dt, expressed as $d^2(E(t))/dt^2$. In one embodiment, the $d^2(E(t))/dt^2$ provides information about reflecting interfaces in the animal tissue.

In one embodiment, the signal trace characteristic further includes a substantially instantaneous phase of the received acoustic energy associated with the given region in the animal tissue, with the phase being expressed as $\Phi(t)=\arctan(g(t)/f(t))$. In one embodiment, the phase $\Phi(t)$ is substantially independent from an amplitude of F(t) and provides information about propagation phase of the acoustic energy from the given region in the animal tissue. In one embodiment, the signal trace characteristic further includes a substantially instantaneous frequency of the received acoustic energy associated with the given region in the animal tissue, with the frequency being expressed as $\omega(t)=d(\Phi(t))/dt$. In one embodiment, the signal trace characteristic further includes a substantially instantaneous acceleration of the received acoustic energy associated with the given region in the animal tissue, with the acceleration being expressed as $a(t)=d\omega(t)/dt$.

In one embodiment, the signal trace characteristic further includes a mean frequency $\omega_{mean}(t)$ of the received acoustic energy associated with the given region in the animal tissue, with the mean frequency being obtained by a method that includes determining a Fourier transform $F(\omega)$ of the function F(t); determining an autocorrelation function $P(\omega)$ by a relationship $P(\omega)=F(\omega)F^*(\omega)$, where $F^*(\omega)$ includes a complex conjugate of $F(\omega)$; determining a normalized autocorrelation function A(t) by a relationship $$A(t) = \int_{\omega=0}^{\infty} P(\omega)\exp(i\omega t)d\omega \bigg/ \int_{\omega=0}^{\infty} P(\omega)d\omega;$$

and determining the mean frequency $\omega_{mean}$ by a relationship $$\omega_{mean}(t) = dA(t)/dt = -i\int_{\omega=0}^{\infty} \omega P(\omega)\exp(i\omega t)d\omega \bigg/ \int_{\omega=0}^{\infty} P(\omega)d\omega.$$

In one embodiment, the signal trace characteristic further includes a thin-layer indicator parameter determined by a relationship $\omega(t)-\omega_{mean}(t)$. In one embodiment, the signal trace characteristic further includes an acceleration of the received acoustic energy associated with the given region in the animal tissue, the acceleration determined by a relationship $|d^2A(t)/dt^2|$. In one embodiment, the signal trace characteristic further includes a centroid frequency $\omega_c$ of a power spectrum by a relationship $$\omega_c = \int_{\omega=0}^{\infty} \omega P(\omega)d\omega \bigg/ \int_{\omega=0}^{\infty} P(\omega)d\omega.$$

In one embodiment, the signal trace characteristic further includes a variance $\omega_v$ to the centroid frequency $\omega_c$ by a relationship $$\omega_v = \int_{\omega=0}^{\infty} (\omega - \omega_c)^2 P(\omega)d\omega \bigg/ \int_{\omega=0}^{\infty} P(\omega)d\omega.$$

In one embodiment, the signal trace characteristic further includes a root-mean-square frequency $\omega_{RMS}$ by a relationship $$\omega_{RMS} = sqrt\left[\int_{\omega=0}^{\infty} \omega^2 P(\omega)d\omega \bigg/ \int_{\omega=0}^{\infty} P(\omega)d\omega\right].$$

In one embodiment where the tissue attribute includes the spatial characteristic, the spatial characteristic includes information about propagation number k associated with the received acoustic energy. In one embodiment, the spatial characteristic further includes a longitudinal component $k_z=(\omega/v)\cos\theta$ and a transverse component $k_t=(\omega/v)\sin\theta$ of the propagation number k, where $\theta$ represents the arrival angle associated with the received acoustic energy.

In one embodiment, the spatial characteristic further includes a time gradient dt/dx along a selected transverse direction x. In one embodiment, the time gradient dt/dx is proportional to $\sin\theta/v$. In one embodiment, the time gradient dt/dx is proportional to $k_x/\omega$, where $\omega$ represents the frequency associated with the received acoustic energy. In one embodiment, the frequency $\omega$ is estimated by a centroid frequency $\omega_c$ associated with the received acoustic energy. In one embodiment, the frequency $\omega$ is estimated by an autocorrelation function A(t) associated with the received acoustic energy, evaluated at one time lag, so that $\omega=\arg|A(1)|$.

In one embodiment, the spatial characteristic further includes a time gradient dt/dy along a selected transverse direction y that is substantially perpendicular to the direction x. In one embodiment, the spatial characteristic further includes an azimuthal time gradient expressed as $\Delta\Phi=\arctan(dt/dy, dt/dx)$. In one embodiment, the spatial characteristic further includes a transverse time gradient expressed as $\Delta T=sqrt[(dt/dx)^2+(dt/dy)^2]$. In one embodiment, the spatial characteristic further includes a lateral continuity estimated as $\Delta^2 T=sqrt[(d^2t/dx^2)^2+(d^2t/dy^2)^2]$.

In one embodiment, the method further includes performing the processing of the electrical signal at one or more ranges of frequency associated with the electrical signal. In one embodiment, processing at the plurality of ranges of frequency includes a spectral decomposition analysis. In one embodiment, the method further includes imaging with ultrasound a region of interest of an animal, with the region of interest having a plurality of voxels, with each of the voxels having a value of the attribute at selected one of the one or more ranges of frequency; determining the value of the attribute for each of the plurality of voxels; and displaying simultaneously on a display the values of the attribute for the plurality of voxels.

In one embodiment, the method further includes classifying the attribute based on its value. In one embodiment, the method further includes generating a result value based on the classifying of the attribute. In one embodiment, the classifying of the attribute and the generating of the result are performed substantially automatically.

The foregoing features with respect to the animal tissue can also be applied to materials, where another embodiment of the present teachings relates to a method for determining an attribute of a material using acoustic energy. The method includes receiving acoustic energy that has been reflected from the material. The method further includes generating an electrical signal from the received acoustic energy. The method further includes processing the electrical signal so as to generate a value of the attribute of the material, with the attribute being selected from the group consisting of an amplitude-variations-with-offset characteristic and a signal trace characteristic. The method further includes registering the value of the attribute in a computer storage.

Another embodiment of the present teachings relates to a device for determining an attribute of an animal tissue using acoustic energy. The device includes an acoustic receiver module that receives acoustic energy that has been reflected from the animal tissue, and outputs an electrical signal based on the received acoustic energy. The device further includes a processor that is configured so as to process the signal and generate a value of the attribute of the animal tissue, the attribute having at least one of an amplitude-variations-with-offset characteristic and a signal trace characteristic. The device further includes a computer storage configured so as to store the value of the attribute of the animal tissue.

In one embodiment, the tissue attribute includes the amplitude-variations-with-offset characteristic. In one embodiment, the tissue attribute includes the signal trace characteristic. In one embodiment, the tissue attribute further includes a spatial characteristic.

In one embodiment where the tissue attribute includes the amplitude-variations-with-offset characteristic, the amplitude-variations-with-offset characteristic includes a plot of a plurality of values corresponding to reflection amplitudes R of the received acoustic energy versus values corresponding to respective reflection angles $\theta$ of the reflection amplitudes, with the reflection angles $\theta$ being with respect to a layer in the animal tissue.

In one embodiment, the amplitude-variations-with-offset characteristic includes a functional relationship R estimated from an R versus $\theta$ plot.

In one embodiment, the functional relationship R includes a relationship $R(\theta)=A+B\sin^2\theta+C\sin^2\theta\tan^2\theta$ where parameters A, B, and C are constants that can be estimated from the R versus $\theta$ plot. In one embodiment, the process is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(4A-9B+5C)/8$ with an assumption that velocity $V_P$ of the compressional component is approximately three times that of velocity $V_S$ of the shear component in the animal tissue.

In another embodiment, the amplitude-variations-with-offset characteristic includes a functional relationship estimated from an R versus $\sin^2\theta$ plot. In one embodiment, the functional relationship R includes a relationship $R(\theta)=A+B\sin^2\theta$, where parameters A and B estimated from the R versus $\sin^2\theta$ plot, with the A being representative of an intercept, and B being representative of a slope of a linear relationship estimated between R and $\sin^2\theta$. In one embodiment, the processor is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(A-B)/2$ with an assumption that velocity $V_P$ of the compressional component is approximately twice that of velocity $V_S$ of the shear component in the animal tissue.

In one embodiment, the processor is further configured so as to invert reflectivity values $R_{P0}$ and $R_{S0}$ so as to obtain estimated values of impedance $Z_P$ and $Z_S$ respectively corresponding to compressional and shear components of the animal tissue. In one embodiment, the processor is further configured so as to estimate one or more elastic properties of the animal tissue based on the estimated impedance values $Z_P$ and $Z_S$. In one embodiment, the one or more elastic properties include a rigidity parameter $\mu$ that corresponds to resistance to shear deformation, and estimated by a relationship $\mu=Z_S^2/\rho$, where $\rho$ represents an estimate of the density of the animal tissue. In one embodiment, the one or more elastic properties further include an elastic parameter $\lambda$ that is sensitive to fluid content of the animal tissue, with the elastic parameter $\lambda$ being estimated by a relationship $\lambda=(Z_P^2-2Z_S^2)/\rho$. In one embodiment, the one or more elastic properties further include a parameter $\kappa$ that corresponds to incompressibility or bulk modulus of the animal tissue, with the parameter $\kappa$ being estimated by a relationship $\kappa=\lambda+(2/3)\mu$.

In one embodiment where the tissue attribute includes the signal trace characteristic, the signal trace characteristic includes a complex function $F(t)=f(t)+ig(t)$, where $f(t)$ includes a real part of $F(t)$ and represents the electrical signal corresponding to a given region in the animal tissue, and $g(t)$ includes an imaginary part of $F(t)$ and represents a Hilbert transform of $f(t)$.

In one embodiment, the signal trace characteristic further includes a modulus $E(t)$ of the complex function $F(t)$ expressed as $E(t)=(f^2(t)+g^2(t))^{1/2}$. In one embodiment, the $E(t)$ represents an envelope of the electrical signal. In one embodiment, square of the $E(t)$ represents a value corresponding to a substantially instantaneous energy associated with the received acoustic energy. In one embodiment, the signal trace characteristic further includes a rate of change of the $E(t)$ with respect to time, expressed as $d(E(t))/dt$. In one embodiment, the $d(E(t))/dt$ provides information about absorption effects in the animal tissue. In one embodiment, the signal trace characteristic further includes a rate of change of the $d(E(t))/dt$, expressed as $d^2(E(t))/dt^2$. In one embodiment, the $d^2(E(t))/dt^2$ provides information about reflecting interfaces in the animal tissue.

In one embodiment, the signal trace characteristic further includes a substantially instantaneous phase of the received acoustic energy associated with the given region in the animal tissue, with the phase being expressed as $\Phi(t)=\arctan(g(t)/f(t))$. In one embodiment, the phase $\Phi(t)$ is substantially independent from an amplitude of $F(t)$ and provides information about propagation phase of the acoustic energy from the given region in the animal tissue. In one embodiment, the signal trace characteristic further includes a substantially instantaneous frequency of the received acoustic energy associated with the given region in the animal tissue, with the frequency being expressed as $\omega(t)=d(\Phi(t))/dt$. In one embodiment, the signal trace characteristic further includes a substantially instantaneous acceleration of the received acoustic energy associated with the given region in the animal tissue, with the acceleration being expressed as $a(t)=d\omega(t)/dt$.

In one embodiment, the signal trace characteristic further includes a mean frequency $\omega_{mean}(t)$ of the received acoustic energy associated with the given region in the animal tissue, with the mean frequency being obtained by a method that includes determining a Fourier transform $F(\omega)$ of the function $F(t)$; determining an autocorrelation function $P(\omega)$ by a relationship $P(\omega)=F(\omega)F^*(\omega)$, where $F^*(\omega)$ includes a complex conjugate of $F(\omega)$; determining a normalized autocorrelation function $A(t)$ by a relationship $$A(t) = \int_{\omega=0}^{\infty} P(\omega)\exp(i\omega t)d\omega \bigg/ \int_{\omega=0}^{\infty} P(\omega)d\omega;$$

and determining the mean frequency $\omega_{mean}$ by a relationship $$\omega_{mean}(t) = dA(t)/dt = -i\int_{\omega=0}^{\infty} \omega P(\omega)\exp(i\omega t)d\omega \bigg/ \int_{\omega=0}^{\infty} P(\omega)d\omega.$$

In one embodiment, the signal trace characteristic further includes a thin-layer indicator parameter determined by a relationship $\omega(t) - \omega_{mean}(t)$. In one embodiment, the signal trace characteristic further includes an acceleration of the received acoustic energy associated with the given region in the animal tissue, the acceleration determined by a relationship $|d^2A(t)/dt^2|$. In one embodiment, the signal trace characteristic further includes a centroid frequency $\omega_c$ of a power spectrum by a relationship $$\omega_c = \int_{\omega=0}^{\infty} \omega P(\omega)d\omega \bigg/ \int_{\omega=0}^{\infty} P(\omega)d\omega.$$

In one embodiment, the signal trace characteristic further includes a variance $\omega_v$ to the centroid frequency $\omega_c$ by a relationship $$\omega_v = \int_{\omega=0}^{\infty} (\omega - \omega_c)^2 P(\omega)d\omega \bigg/ \int_{\omega=0}^{\infty} P(\omega)d\omega.$$

In one embodiment, the signal trace characteristic further includes a root-mean-square frequency $\omega_{RMS}$ by a relationship $$\omega_{RMS} = sqrt\left[\int_{\omega=0}^{\infty} \omega^2 P(\omega)d\omega \bigg/ \int_{\omega=0}^{\infty} P(\omega)d\omega\right].$$

In one embodiment where the tissue attribute includes the spatial characteristic, the spatial characteristic includes information about propagation number k associated with the received acoustic energy. In one embodiment, the spatial characteristic further includes a longitudinal component $k_z = (\omega/v)\cos\theta$ and a transverse component $k_t = (\omega/v)\sin\theta$ of the propagation number k, where $\theta$ represents the arrival angle associated with the received acoustic energy.

In one embodiment, the spatial characteristic further includes a time gradient dt/dx along a selected transverse direction x. In one embodiment, the time gradient dt/dx is proportional to $\sin\theta/v$. In one embodiment, the time gradient dt/dx is proportional to $k_x/\omega$, where $\omega$ represents the frequency associated with the received acoustic energy. In one embodiment, the frequency $\omega$ is estimated by a centroid frequency $\omega_c$ associated with the received acoustic energy. In one embodiment, the frequency $\omega$ is estimated by an autocorrelation function $A(t)$ associated with the received acoustic energy, evaluated at one time lag, so that $\omega = \arg|A(1)|$.

In one embodiment, the spatial characteristic further includes a time gradient dt/dy along a selected transverse direction y that is substantially perpendicular to the direction x. In one embodiment, the spatial characteristic further includes an azimuthal time gradient expressed as $\Delta\Phi = \arctan(dt/dy, dt/dx)$. In one embodiment, the spatial characteristic further includes a transverse time gradient expressed as $\Delta T = sqrt[(dt/dx)^2 + (dt/dy)^2]$. In one embodiment, the spatial characteristic further includes a lateral continuity estimated as $\Delta^2 T = sqrt[(d^2t/dx^2)^2 + (d^2t/dy^2)^2]$.

In one embodiment, the processor is further configured so as to perform the processing of the electrical signal at one or more ranges of frequency associated with the electrical signal. In one embodiment, processing at the plurality of ranges of frequency includes a spectral decomposition analysis. In one embodiment, the device further includes a display component that is configured so as to display simultaneously values of the attribute that correspond to a plurality of voxels contained within a region of interest of the animal.

In one embodiment, the processor is further configured so as to classify the attribute based on its value. In one embodiment, the processor is further configured so as to generate a result value based on the classifying of the attribute. In one embodiment, the classifying of the attribute and the generating of the result are performed substantially automatically.

The foregoing features with respect to the animal tissue can also be applied to materials, where another embodiment of the present teachings relates to a device for determining an attribute of a material using acoustic energy. The device includes an acoustic receiver module that receives acoustic energy that has been reflected from the material, and outputs an electrical signal based on the received acoustic energy. The device further includes a processor that is configured so as to process the signal and generate a value of the attribute of the material, the attribute having at least one of an amplitude-variations-with-offset characteristic and a signal trace characteristic. The device further includes a computer storage configured so as to store the value of the attribute of the animal tissue.

Yet another embodiment of the present teachings relates to a method for determining attributes of an animal tissue using acoustic energy. The method includes receiving acoustic energy that has been reflected from the animal tissue. The method further includes generating an electrical signal from the received acoustic energy. The method further includes processing the electrical signal so as to generate values of at least two attributes of the animal tissue, with the attributes being selected from the group consisting of an amplitude-variations-with-offset characteristic, a signal trace characteristic, and a spectral decomposition characteristic. The method further includes registering the values of the at least two attributes in a computer storage.

In one embodiment, the at least two attributes include at least two attributes obtained from the amplitude-variations-with-offset characteristic. In one embodiment, the at least two attributes include at least two attributes obtained from the signal trace characteristic. In one embodiment, the at least two attributes include at least two attributes obtained from the spectral decomposition characteristic. In one embodiment, the at least two attributes include at least one attribute from the amplitude-variations-with-offset characteristic, and at least one attribute from the signal trace characteristic. In one embodiment, the at least two attributes include at least one attribute from the amplitude-variations-with-offset characteristic, and at least one attribute from the spectral decomposition characteristic. In one embodiment, the at least two attributes include at least one attribute from the signal trace characteristic, and at least one attribute from the spectral decomposition characteristic.

In one embodiment, the at least two attributes further include at least one attribute from a spatial characteristic. In one embodiment, the at least two attributes include at least one attribute from the amplitude-variations-with-offset characteristic, and at least one attribute from the spatial characteristic. In one embodiment, the at least two attributes include at least one attribute from the signal trace characteristic, and at least one attribute from the spatial characteristic. In one embodiment, the at least two attributes include at least one attribute from the spatial characteristic, and at least one attribute from the spectral decomposition characteristic.

In one embodiment, registering the values of the at least two of the attributes includes providing an index for each attribute, with the index having information about a plurality of voxels in a region of interest in the animal tissue. In one embodiment, the method further includes displaying a plot of values corresponding to a first set of two of the at least two attributes based on the registered values. In one embodiment, the method further includes selecting a portion of the displayed plot so as to select one or more values corresponding to the first set of two attributes, with the selected one or more values having corresponding indices. In one embodiment, the method further includes displaying a plot of values corresponding to a second set of two of the at least two attributes, with the values of the second set corresponding to the indices of the selected one or more values from the first set of two attributes.

In one embodiment, the tissue attribute includes the amplitude-variations-with-offset characteristic. In one embodiment, the tissue attribute includes the signal trace characteristic. In one embodiment, the tissue attribute includes the spatial characteristic. In one embodiment, the tissue attribute includes the spectral decomposition characteristic.

In one embodiment where the tissue attribute includes the amplitude-variations-with-offset characteristic, the amplitude-variations-with-offset characteristic includes a plot of a plurality of values corresponding to reflection amplitudes R of the received acoustic energy versus values corresponding to respective reflection angles $\theta$ of the reflection amplitudes, with the reflection angles $\theta$ being with respect to a layer in the animal tissue.

In one embodiment, the amplitude-variations-with-offset characteristic includes a functional relationship R estimated from an R versus $\theta$ plot.

In one embodiment, the functional relationship R includes a relationship $R(\theta)=A+B \sin^2\theta+C \sin^2\theta \tan^2\theta$ where parameters A, B, and C are constants that can be estimated from the R versus $\theta$ plot. In one embodiment, the method further includes estimating values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(4A-9B+5C)/8$ with an assumption that velocity $V_P$ of the compressional component is approximately three times that of velocity $V_S$ of the shear component in the animal tissue.

In another embodiment, the amplitude-variations-with-offset characteristic includes a functional relationship estimated from an R versus $\sin^2\theta$ plot. In one embodiment, the functional relationship R includes a relationship $R(\theta)=A+B \sin^2\theta$, where parameters A and B estimated from the R versus $\sin^2\theta$ plot, with the A being representative of an intercept, and B being representative of a slope of a linear relationship estimated between R and $\sin^2\theta$. In one embodiment, the method further includes estimating values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(A-B)/2$ with an assumption that velocity $V_P$ of the compressional component is approximately twice that of velocity $V_S$ of the shear component in the animal tissue.

In one embodiment, the method further includes inverting reflectivity values $R_{P0}$ and $R_{S0}$ so as to obtain estimated values of impedance $Z_P$ and $Z_S$ respectively corresponding to compressional and shear components of the animal tissue. In one embodiment, the method further includes estimating one or more elastic properties of the animal tissue based on the estimated impedance values $Z_P$ and $Z_S$. In one embodiment, the one or more elastic properties include a rigidity parameter $\mu$ that corresponds to resistance to shear deformation, and estimated by a relationship $\mu=Z_S^2/\rho$, where $\rho$ represents an estimate of the density of the animal tissue. In one embodiment, the one or more elastic properties further include an elastic parameter $\lambda$ that is sensitive to fluid content of the animal tissue, with the elastic parameter $\lambda$ being estimated by a relationship $\lambda=(Z_P^2-2Z_S^2)/\rho$. In one embodiment, the one or more elastic properties further include a parameter $\kappa$ that corresponds to incompressibility or bulk modulus of the animal tissue, with the parameter $\kappa$ being estimated by a relationship $\kappa=\lambda+(2/3)\mu$.

In one embodiment where the tissue attribute includes the signal trace characteristic, the signal trace characteristic includes a complex function $F(t)=f(t)+ig(t)$, where $f(t)$ includes a real part of $F(t)$ and represents the electrical signal corresponding to a given region in the animal tissue, and $g(t)$ includes an imaginary part of $F(t)$ and represents a Hilbert transform of $f(t)$.

In one embodiment, the signal trace characteristic further includes a modulus $E(t)$ of the complex function $F(t)$ expressed as $E(t)=(f^2(t)+g^2(t))^{1/2}$. In one embodiment, the $E(t)$ represents an envelope of the electrical signal. In one embodiment, square of the $E(t)$ represents a value corresponding to a substantially instantaneous energy associated with the received acoustic energy. In one embodiment, the signal trace characteristic further includes a rate of change of the $E(t)$ with respect to time, expressed as $d(E(t))/dt$. In one embodiment, the $d(E(t))/dt$ provides information about absorption effects in the animal tissue. In one embodiment, the signal trace characteristic further includes a rate of change of the $d(E(t))/dt$, expressed as $d^2(E(t))/dt^2$. In one embodiment, the $d^2(E(t))/dt^2$ provides information about reflecting interfaces in the animal tissue.

In one embodiment, the signal trace characteristic further includes a substantially instantaneous phase of the received acoustic energy associated with the given region in the animal tissue, with the phase being expressed as $\Phi(t)=\arctan(g(t)/f(t))$. In one embodiment, the phase $\Phi(t)$ is substantially independent from an amplitude of $F(t)$ and provides information about propagation phase of the acoustic energy from the given region in the animal tissue. In one embodiment, the signal trace characteristic further includes a substantially instantaneous frequency of the received acoustic energy associated with the given region in the animal tissue, with the frequency being expressed as $\omega(t)=d(\Phi(t))/dt$. In one embodiment, the signal trace characteristic further includes a substantially instantaneous acceleration of the received acoustic energy associated with the given region in the animal tissue, with the acceleration being expressed as $a(t)=d\omega(t)/dt$.

In one embodiment, the signal trace characteristic further includes a mean frequency $\omega_{mean}(t)$ of the received acoustic energy associated with the given region in the animal tissue, with the mean frequency being obtained by a method that includes determining a Fourier transform $F(\omega)$ of the function $F(t)$; determining an autocorrelation function $P(\omega)$ by a relationship $P(\omega)=F(\omega)F^*(\omega)$, where $F^*(\omega)$ includes a complex conjugate of $F(\omega)$; determining a normalized autocorrelation function $A(t)$ by a relationship $$A(t) = \int_{\omega=0}^{\infty} P(\omega)\exp(i\omega t)d\omega \bigg/ \int_{\omega=0}^{\infty} P(\omega)d\omega;$$

and determining the mean frequency $\omega_{mean}$ by a relationship $$\omega_{mean}(t) = dA(t)/dt = -i \int_{\omega=0}^{\infty} \omega P(\omega)\exp(i\omega t)d\omega \bigg/ \int_{\omega=0}^{\infty} P(\omega)d\omega.$$

In one embodiment, the signal trace characteristic further includes a thin-layer indicator parameter determined by a relationship $\omega(t)-\omega_{mean}(t)$. In one embodiment, the signal trace characteristic further includes an acceleration of the received acoustic energy associated with the given region in the animal tissue, the acceleration determined by a relationship $|d^2A(t)/dt^2|$. In one embodiment, the signal trace characteristic further includes a centroid frequency $\omega_c$ of a power spectrum by a relationship $$\omega_c = \int_{\omega=0}^{\infty} \omega P(\omega)d\omega \bigg/ \int_{\omega=0}^{\infty} P(\omega)d\omega.$$

In one embodiment, the signal trace characteristic further includes a variance $\omega_v$ to the centroid frequency $\omega_c$ by a relationship $$\omega_v = \int_{\omega=0}^{\infty} (\omega - \omega_c)^2 P(\omega)d\omega \bigg/ \int_{\omega=0}^{\infty} P(\omega)d\omega.$$

In one embodiment, the signal trace characteristic further includes a root-mean-square frequency $\omega_{RMS}$ by a relationship $$\omega_{RMS} = sqrt\bigg[\int_{\omega=0}^{\infty} \omega^2 P(\omega)d\omega \bigg/ \int_{\omega=0}^{\infty} P(\omega)d\omega\bigg].$$

In one embodiment where the tissue attribute includes the spatial characteristic, the spatial characteristic includes information about propagation number k associated with the received acoustic energy. In one embodiment, the spatial characteristic further includes a longitudinal component $k_z=(\omega/v)\cos\theta$ and a transverse component $k_t=(\omega/v)\sin\theta$ of the propagation number k, where $\theta$ represents the arrival angle associated with the received acoustic energy.

In one embodiment, the spatial characteristic further includes a time gradient dt/dx along a selected transverse direction x. In one embodiment, the time gradient dt/dx is proportional to $\sin\theta/v$. In one embodiment, the time gradient dt/dx is proportional to $k_x/\omega$, where $\omega$ represents the frequency associated with the received acoustic energy. In one embodiment, the frequency $\omega$ is estimated by a centroid frequency $\omega_c$ associated with the received acoustic energy. In one embodiment, the frequency $\omega$ is estimated by an autocorrelation function $A(t)$ associated with the received acoustic energy, evaluated at one time lag, so that $\omega=\arg|A(1)|$.

In one embodiment, the spatial characteristic further includes a time gradient dt/dy along a selected transverse direction y that is substantially perpendicular to the direction x. In one embodiment, the spatial characteristic further includes an azimuthal time gradient expressed as $\Delta\Phi=\arctan(dt/dy, dt/dx)$. In one embodiment, the spatial characteristic further includes a transverse time gradient expressed as $\Delta T=sqrt[(dt/dx)^2+(dt/dy)^2]$. In one embodiment, the spatial characteristic further includes a lateral continuity estimated as $\Delta^2 T=sqrt[(d^2t/dx^2)^2+(d^2t/dy^2)^2]$.

In one embodiment, the method further includes performing the processing of the electrical signal at one or more ranges of frequency associated with the electrical signal. In one embodiment, processing at the plurality of ranges of frequency includes a spectral decomposition analysis. In one embodiment, the method further includes imaging with ultrasound a region of interest of an animal, with the region of interest having a plurality of voxels, with each of the voxels having a value of the attribute at selected one of the one or more ranges of frequency; determining the value of the attribute for each of the plurality of voxels; and displaying simultaneously on a display the values of the attribute for the plurality of voxels.

In one embodiment, the method further includes classifying the attribute based on its value. In one embodiment, the method further includes generating a result value based on the classifying of the attribute. In one embodiment, the classifying of the attribute and the generating of the result are performed substantially automatically.

The foregoing features with respect to the animal tissue can also be applied to materials, where another embodiment of the present teachings relates to a method for determining attributes of a material using acoustic energy. The method includes receiving acoustic energy that has been reflected from the material. The method further includes generating an electrical signal from the received acoustic energy. The method further includes processing the electrical signal so as to generate values of at least two attributes of the material, with the attributes being selected from the group consisting of an amplitude-variations-with-offset characteristic, a signal trace characteristic, and a spectral decomposition characteristic. The method further includes registering the values of the at least two attributes in a computer storage.

Yet another embodiment of the present teachings relates to a device for determining at least two attributes of an animal tissue using acoustic energy. The device includes an acoustic receiver module that receives acoustic energy that has been reflected from the animal tissue, and outputs an electrical signal based on the received acoustic energy. The device further includes a processor that is configured so as to process the signal so as to generate values of the at least two attributes of the animal tissue, with the attributes being selected from the group consisting of an amplitude-variations-with-offset characteristic, a signal trace characteristic, and a spectral decomposition characteristic. The device further includes a computer storage configured so as to store the values of at the least two attributes of the animal tissue.

In one embodiment, the at least two attributes include at least two attributes obtained from the amplitude-variations-with-offset characteristic. In one embodiment, the at least two attributes include at least two attributes obtained from the signal trace characteristic. In one embodiment, the at least two attributes include at least two attributes obtained from the spectral decomposition characteristic. In one embodiment, the at least two attributes include at least one attribute from the amplitude-variations-with-offset characteristic, and at least one attribute from the signal trace characteristic. In one embodiment, the at least two attributes include at least one attribute from the amplitude-variations-with-offset characteristic, and at least one attribute from the spectral decomposition characteristic. In one embodiment, the at least two attributes include at least one attribute from the signal trace characteristic, and at least one attribute from the spectral decomposition characteristic.

In one embodiment, the at least two attributes further include at least one attribute from a spatial characteristic. In one embodiment, the at least two attributes include at least one attribute from the amplitude-variations-with-offset characteristic, and at least one attribute from the spatial characteristic. In one embodiment, the at least two attributes include at least one attribute from the signal trace characteristic, and at least one attribute from the spatial characteristic. In one embodiment, the at least two attributes include at least one attribute from the spatial characteristic, and at least one attribute from the spectral decomposition characteristic.

In one embodiment, the values of the at least two of the attributes includes information about an index for each attribute, with the index having information about a plurality of voxels in a region of interest in the animal tissue. In one embodiment, the device further includes a display component that is configured so as to plot values corresponding to a first set of two of the at least two attributes based on the registered values. In one embodiment, the display component is further configured so as to allow selection of a portion of the displayed plot so as to select one or more values corresponding to the first set of two attributes, with the selected one or more values having corresponding indices. In one embodiment, the display component is further configured so as to display a plot of values corresponding to a second set of two of the at least two attributes, with the values of the second set corresponding to the indices of the selected one or more values from the first set of two attributes.

In one embodiment, the tissue attribute includes the amplitude-variations-with-offset characteristic. In one embodiment, the tissue attribute includes the signal trace characteristic. In one embodiment, the tissue attribute includes the spatial characteristic. In one embodiment, the tissue attribute includes the spectral decomposition characteristic.

In one embodiment where the tissue attribute includes the amplitude-variations-with-offset characteristic, the amplitude-variations-with-offset characteristic includes a plot of a plurality of values corresponding to reflection amplitudes R of the received acoustic energy versus values corresponding to respective reflection angles $\theta$ of the reflection amplitudes, with the reflection angles $\theta$ being with respect to a layer in the animal tissue.

In one embodiment, the amplitude-variations-with-offset characteristic includes a functional relationship R estimated from an R versus $\theta$ plot.

In one embodiment, the functional relationship R includes a relationship $R(\theta)=A+B \sin^2\theta+C \sin^2\theta \tan^2\theta$ where parameters A, B, and C are constants that can be estimated from the R versus $\theta$ plot. In one embodiment, the process is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(4A-9B+5C)/8$ with an assumption that velocity $V_P$ of the compressional component is approximately three times that of velocity $V_S$ of the shear component in the animal tissue.

In another embodiment, the amplitude-variations-with-offset characteristic includes a functional relationship estimated from an R versus $\sin^2\theta$ plot. In one embodiment, the functional relationship R includes a relationship $R(\theta)=A+B \sin 2\theta$, where parameters A and B estimated from the R versus $\sin^2\theta$ plot, with the A being representative of an intercept, and B being representative of a slope of a linear relationship estimated between R and $\sin^2\theta$. In one embodiment, the processor is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(A-B)/2$ with an assumption that velocity $V_P$ of the compressional component is approximately twice that of velocity $V_S$ of the shear component in the animal tissue.

In one embodiment, the processor is further configured so as to invert reflectivity values $R_{P0}$ and $R_{S0}$ so as to obtain estimated values of impedance $Z_P$ and $Z_S$ respectively corresponding to compressional and shear components of the animal tissue. In one embodiment, the processor is further configured so as to estimate one or more elastic properties of the animal tissue based on the estimated impedance values $Z_P$ and $Z_S$. In one embodiment, the one or more elastic properties include a rigidity parameter $\mu$ that corresponds to resistance to shear deformation, and estimated by a relationship $\mu=Z_S^2/\rho$, where $\rho$ represents an estimate of the density of the animal tissue. In one embodiment, the one or more elastic properties further include an elastic parameter $\lambda$ that is sensitive to fluid content of the animal tissue, with the elastic parameter $\lambda$ being estimated by a relationship $\lambda=(Z_P^2-2Z_S^2)/\rho$. In one embodiment, the one or more elastic properties further include a parameter $\kappa$ that corresponds to incompressibility or bulk modulus of the animal tissue, with the parameter $\kappa$ being estimated by a relationship $\kappa=\lambda+(2/3)\mu$.

In one embodiment where the tissue attribute includes the signal trace characteristic, the signal trace characteristic includes a complex function $F(t)=f(t)+ig(t)$, where $f(t)$ includes a real part of $F(t)$ and represents the electrical signal corresponding to a given region in the animal tissue, and $g(t)$ includes an imaginary part of $F(t)$ and represents a Hilbert transform of $f(t)$.

In one embodiment, the signal trace characteristic further includes a modulus $E(t)$ of the complex function $F(t)$ expressed as $E(t)=(f^2(t)+g^2(t))^{1/2}$. In one embodiment, the $E(t)$ represents an envelope of the electrical signal. In one embodiment, square of the $E(t)$ represents a value corresponding to a substantially instantaneous energy associated with the received acoustic energy. In one embodiment, the signal trace characteristic further includes a rate of change of the $E(t)$ with respect to time, expressed as $d(E(t))/dt$. In one embodiment, the $d(E(t))/dt$ provides information about absorption effects in the animal tissue. In one embodiment, the signal trace characteristic further includes a rate of change of the $d(E(t))/dt$, expressed as $d^2(E(t))/dt^2$. In one embodiment, the $d^2(E(t))/dt^2$ provides information about reflecting interfaces in the animal tissue.

In one embodiment, the signal trace characteristic further includes a substantially instantaneous phase of the received acoustic energy associated with the given region in the animal tissue, with the phase being expressed as $\Phi(t)=\arctan(g(t)/f(t))$. In one embodiment, the phase $\Phi(t)$ is substantially independent from an amplitude of $F(t)$ and provides information about propagation phase of the acoustic energy from the given region in the animal tissue. In one embodiment, the signal trace characteristic further includes a substantially instantaneous frequency of the received acoustic energy associated with the given region in the animal tissue, with the frequency being expressed as $\omega(t)=d(\Phi D(t))/dt$. In one embodiment, the signal trace characteristic further includes a substantially instantaneous acceleration of the received acoustic energy associated with the given region in the animal tissue, with the acceleration being expressed as $a(t)=d\omega(t)/dt$.

In one embodiment, the signal trace characteristic further includes a mean frequency $\omega_{mean}(t)$ of the received acoustic energy associated with the given region in the animal tissue, with the mean frequency being obtained by a method that includes determining a Fourier transform $F(\omega)$ of the function $F(t)$; determining an autocorrelation function $P(\omega)$ by a relationship $P(\omega)=F(\omega)F^*(\omega)$, where $F^*(\omega)$ includes a complex conjugate of $F(\omega)$; determining a normalized autocorrelation function $A(t)$ by a relationship $$A(t) = \int_{\omega=0}^{\infty} P(\omega)\exp(i\omega t)d\omega \bigg/ \int_{\omega=0}^{\infty} P(\omega)d\omega;$$

and determining the mean frequency $\omega_{mean}$ by a relationship $$\omega_{mean}(t) = dA(t)/dt = -i\int_{\omega=0}^{\infty} \omega P(\omega)\exp(i\omega t)d\omega \bigg/ \int_{\omega=0}^{\infty} P(\omega)d\omega.$$

In one embodiment, the signal trace characteristic further includes a thin-layer indicator parameter determined by a relationship $\omega(t)-\omega_{mean}(t)$. In one embodiment, the signal trace characteristic further includes an acceleration of the received acoustic energy associated with the given region in the animal tissue, the acceleration determined by a relationship $|d^2A(t)/dt^2|$. In one embodiment, the signal trace characteristic further includes a centroid frequency $\omega_c$ of a power spectrum by a relationship $$\omega_c = \int_{\omega=0}^{\infty} \omega P(\omega)d\omega \bigg/ \int_{\omega=0}^{\infty} P(\omega)d\omega.$$

In one embodiment, the signal trace characteristic further includes a variance $\omega_v$ to the centroid frequency $\omega_c$ by a relationship $$\omega_v = \int_{\omega=0}^{\infty} (\omega - \omega_c)^2 P(\omega)d\omega \bigg/ \int_{\omega=0}^{\infty} P(\omega)d\omega.$$

In one embodiment, the signal trace characteristic further includes a root-mean-square frequency $\omega_{RMS}$ by a relationship $$\omega_{RMS} = sqrt\left[\int_{\omega=0}^{\infty} \omega^2 P(\omega)d\omega \bigg/ \int_{\omega=0}^{\infty} P(\omega)d\omega\right].$$

In one embodiment where the tissue attribute includes the spatial characteristic, the spatial characteristic includes information about propagation number k associated with the received acoustic energy. In one embodiment, the spatial characteristic further includes a longitudinal component $k_z=(\omega/v)\cos\theta$ and a transverse component $k_r=(\omega/v)\sin\theta$ of the propagation number k, where $\theta$ represents the arrival angle associated with the received acoustic energy.

In one embodiment, the spatial characteristic further includes a time gradient dt/dx along a selected transverse direction x. In one embodiment, the time gradient dt/dx is proportional to $\sin\theta/v$. In one embodiment, the time gradient dt/dx is proportional to $k_x/\omega$, where $\omega$ represents the frequency associated with the received acoustic energy. In one embodiment, the frequency $\omega$ is estimated by a centroid frequency $\omega_c$ associated with the received acoustic energy. In one embodiment, the frequency $\omega$ is estimated by an autocorrelation function $A(t)$ associated with the received acoustic energy, evaluated at one time lag, so that $\omega=arg|A(1)|$.

In one embodiment, the spatial characteristic further includes a time gradient dt/dy along a selected transverse direction y that is substantially perpendicular to the direction x. In one embodiment, the spatial characteristic further includes an azimuthal time gradient expressed as $\Delta\Phi=arctan(dt/dy, dt/dx)$. In one embodiment, the spatial characteristic further includes a transverse time gradient expressed as $\Delta T=sqrt[(dt/dx)^2+(dt/dy)^2]$. In one embodiment, the spatial characteristic further includes a lateral continuity estimated as $\Delta^2 T=sqrt[(d^2t/dx^2)^2+(d^2t/dy^2)^2]$.

In one embodiment, the processor is further configured so as to perform the processing of the electrical signal at one or more ranges of frequency associated with the electrical signal. In one embodiment, processing at the plurality of ranges of frequency includes a spectral decomposition analysis. In one embodiment, the device further includes a display component that is configured so as to display simultaneously values of the attribute that correspond to a plurality of voxels contained within a region of interest of the animal.

In one embodiment, the processor is further configured so as to classify the attribute based on its value. In one embodiment, the processor is further configured so as to generate a result value based on the classifying of the attribute. In one embodiment, the classifying of the attribute and the generating of the result are performed substantially automatically.

The foregoing features with respect to the animal tissue can also be applied to materials, where another embodiment of the present teachings relates to a device for determining at least two attributes of a material using acoustic energy. The device includes an acoustic receiver module that receives acoustic energy that has been reflected from the material, and outputs an electrical signal based on the received acoustic energy. The device further includes a processor that is configured so as to process the signal so as to generate values of the at least two attributes of the material, with the attributes being selected from the group consisting of an amplitude-variations-with-offset characteristic, a signal trace characteristic, and a spectral decomposition characteristic. The device further includes a computer storage configured so as to store the values of at the least two attributes of the material.

Yet another embodiment of the present teachings relates to a device for determining an attribute of an animal tissue using acoustic energy. The device includes a means for receiving acoustic energy that has been reflected from the animal tissue. The device further includes a means for outputting an electrical signal based on the received acoustic energy. The device further includes a means for processing the signal so as to generate a value of the attribute of the animal tissue, with the attribute having at least one of an amplitude-variations-with-offset characteristic, a signal trace characteristic, a spatial characteristic, and a spectral decomposition characteristic. The device further includes a means for storing in a computer-readable medium the value of the attribute of the animal tissue.

In one embodiment, the tissue attribute includes the amplitude-variations-with-offset characteristic. In one embodiment, the tissue attribute includes the signal trace characteristic. In one embodiment, the tissue attribute includes the spatial characteristic. In one embodiment, the tissue attribute includes the spectral decomposition characteristic.

The foregoing features with respect to the animal tissue can also be applied to materials, where another embodiment of the present teachings relates to a device for determining an attribute of a material using acoustic energy. The device includes a means for receiving acoustic energy that has been reflected from the material. The device further includes a means for outputting an electrical signal based on the received acoustic energy. The device further includes a means for processing the signal so as to generate a value of the attribute of the material, with the attribute having at least one of an amplitude-variations-with-offset characteristic, a signal trace characteristic, a spatial characteristic, and a spectral decomposition characteristic. The device further includes a means for storing in a computer-readable medium the value of the attribute of the material.

Yet another embodiment of the present teachings relates to a computer-readable medium having a computer-executable instruction that is configured to process a signal so as to generate values of at least two attributes of an animal tissue, with the at least two attributes being selected from the group consisting of an amplitude-variations-with-offset characteristic, a signal trace characteristic, a spatial characteristic, and a spectral decomposition characteristic. The signal is based on an acoustic energy that has been reflected from the animal tissue.

In one embodiment, the at least two attributes include at least two attributes obtained from the amplitude-variations-with-offset characteristic. In one embodiment, the at least two attributes include at least two attributes obtained from the signal trace characteristic. In one embodiment, the at least two attributes include at least two attributes obtained from the spectral decomposition characteristic. In one embodiment, the at least two attributes include at least one attribute from the amplitude-variations-with-offset characteristic, and at least one attribute from the signal trace characteristic. In one embodiment, the at least two attributes include at least one attribute from the amplitude-variations-with-offset characteristic, and at least one attribute from the spectral decomposition characteristic. In one embodiment, the at least two attributes include at least one attribute from the signal trace characteristic, and at least one attribute from the spectral decomposition characteristic.

In one embodiment, the at least two attributes further include at least one attribute from the spatial characteristic. In one embodiment, the at least two attributes include at least one attribute from the amplitude-variations-with-offset characteristic, and at least one attribute from the spatial characteristic. In one embodiment, the at least two attributes include at least one attribute from the signal trace characteristic, and at least one attribute from the spatial characteristic. In one embodiment, the at least two attributes include at least one attribute from the spatial characteristic, and at least one attribute from the spectral decomposition characteristic.

In one embodiment, the values of the at least two of the attributes includes information about an index for each attribute, with the index having information about a plurality of voxels in a region of interest in the animal tissue.

In one embodiment, the tissue attribute includes the amplitude-variations-with-offset characteristic. In one embodiment, the tissue attribute includes the signal trace characteristic. In one embodiment, the tissue attribute includes the spatial characteristic. In one embodiment, the tissue attribute includes the spectral decomposition characteristic.

In one embodiment where the tissue attribute includes the amplitude-variations-with-offset characteristic, the amplitude-variations-with-offset characteristic includes a plot of a plurality of values corresponding to reflection amplitudes R of the received acoustic energy versus values corresponding to respective reflection angles θ of the reflection amplitudes, with the reflection angles θ being with respect to a layer in the animal tissue.

In one embodiment, the amplitude-variations-with-offset characteristic includes a functional relationship R estimated from an R versus θ plot.

In one embodiment, the functional relationship R includes a relationship $R(\theta)=A+B \sin^2\theta+C \sin^2\theta \tan^2\theta$ where parameters A, B, and C are constants that can be estimated from the R versus θ plot. In one embodiment, the process is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(4A-9B+5C)/8$ with an assumption that velocity $V_P$ of the compressional component is approximately three times that of velocity $V_S$ of the shear component in the animal tissue.

In another embodiment, the amplitude-variations-with-offset characteristic includes a functional relationship estimated from an R versus $\sin^2\theta$ plot. In one embodiment, the functional relationship R includes a relationship $R(\theta)=A+B \sin^2\theta$, where parameters A and B estimated from the R versus $\sin^2\theta$ plot, with the A being representative of an intercept, and B being representative of a slope of a linear relationship estimated between R and $\sin^2\theta$. In one embodiment, the computer-executable instruction is further configured so as to estimate values $R_{P0}$ and $R_{S0}$ respectively corresponding to zero-offset reflectivity of a compressional component of the received acoustic energy and zero-offset reflectivity of a shear component of the received acoustic energy. In one embodiment, $R_{P0}$ and $R_{S0}$ are approximated as $R_{P0}=A$ and $R_{S0}=(A-B)/2$ with an assumption that velocity $V_P$ of the compressional component is approximately twice that of velocity $V_S$ of the shear component in the animal tissue.

In one embodiment, the computer-executable instruction is further configured so as to invert reflectivity values $R_{P0}$ and $R_{S0}$ so as to obtain estimated values of impedance $Z_P$ and $Z_S$ respectively corresponding to compressional and shear components of the animal tissue. In one embodiment, the computer-executable instruction is further configured so as to estimate one or more elastic properties of the animal tissue based on the estimated impedance values $Z_P$ and $Z_S$. In one embodiment, the one or more elastic properties include a rigidity parameter μ that corresponds to resistance to shear deformation, and estimated by a relationship $\mu=Z_S^2/\rho$, where ρ represents an estimate of the density of the animal tissue. In one embodiment, the one or more elastic properties further include an elastic parameter λ that is sensitive to fluid content of the animal tissue, with the elastic parameter λ being estimated by a relationship $\lambda=(Z_P^2-2Z_S^2)/\rho$. In one embodiment, the one or more elastic properties further include a parameter κ that corresponds to incompressibility or bulk modulus of the animal tissue, with the parameter K being estimated by a relationship $\kappa=\lambda+(2/3)\mu$.

In one embodiment where the tissue attribute includes the signal trace characteristic, the signal trace characteristic includes a complex function $F(t)=f(t)+ig(t)$, where f(t) includes a real part of F(t) and represents the electrical signal corresponding to a given region in the animal tissue, and g(t) includes an imaginary part of F(t) and represents a Hilbert transform of f(t).

In one embodiment, the signal trace characteristic further includes a modulus E(t) of the complex function F(t) expressed as $E(t)=(f^2(t)+g^2(t))^{1/2}$. In one embodiment, the E(t) represents an envelope of the electrical signal. In one embodiment, square of the E(t) represents a value corresponding to a substantially instantaneous energy associated with the received acoustic energy. In one embodiment, the signal trace characteristic further includes a rate of change of the E(t) with respect to time, expressed as $d(E(t))/dt$. In one embodiment, the $d(E(t))/dt$ provides information about absorption effects in the animal tissue. In one embodiment, the signal trace characteristic further includes a rate of change of the $d(E(t))/dt$, expressed as $d^2(E(t))/dt^2$. In one embodiment, the $d^2(E(t))/dt^2$ provides information about reflecting interfaces in the animal tissue.

In one embodiment, the signal trace characteristic further includes a substantially instantaneous phase of the received acoustic energy associated with the given region in the animal tissue, with the phase being expressed as $\Phi(t)=\arctan(g(t)/f(t))$. In one embodiment, the phase $\Phi(t)$ is substantially independent from an amplitude of F(t) and provides information about propagation phase of the acoustic energy from the given region in the animal tissue. In one embodiment, the signal trace characteristic further includes a substantially instantaneous frequency of the received acoustic energy associated with the given region in the animal tissue, with the frequency being expressed as $\omega(t)=d(\Phi(t))/dt$. In one embodiment, the signal trace characteristic further includes a substantially instantaneous acceleration of the received acoustic energy associated with the given region in the animal tissue, with the acceleration being expressed as $a(t)=d\omega(t)/dt$.

In one embodiment, the signal trace characteristic further includes a mean frequency $\omega_{mean}(t)$ of the received acoustic energy associated with the given region in the animal tissue, with the mean frequency being obtained by a method that includes determining a Fourier transform $F(\omega)$ of the function F(t); determining an autocorrelation function $P(\omega)$ by a relationship $P(\omega)=F(\omega)F^*(\omega)$, where $F^*(\omega)$ includes a complex conjugate of $F(\omega)$; determining a normalized autocorrelation function A(t) by a relationship $$A(t) = \int_{\omega=0}^{\infty} P(\omega)\exp(i\omega t)d\omega \Big/ \int_{\omega=0}^{\infty} P(\omega)d\omega;$$

and determining the mean frequency $\omega_{mean}$ by a relationship $$\omega_{mean}(t) = d\,A(t)/d\,t = -i\int_{\omega=0}^{\infty} \omega P(\omega)\exp(i\omega t)d\omega \Big/ \int_{\omega=0}^{\infty} P(\omega)d\omega.$$

In one embodiment, the signal trace characteristic further includes a thin-layer indicator parameter determined by a relationship $\omega(t)-\omega_{mean}(t)$. In one embodiment, the signal trace characteristic further includes an acceleration of the received acoustic energy associated with the given region in the animal tissue, the acceleration determined by a relationship $|d^2A(t)/dt^2|$. In one embodiment, the signal trace characteristic further includes a centroid frequency $\omega_c$ of a power spectrum by a relationship $$\omega_c = \int_{\omega=0}^{\infty} \omega P(\omega)d\omega \Big/ \int_{\omega=0}^{\infty} P(\omega)d\omega.$$

In one embodiment, the signal trace characteristic further includes a variance $\omega_v$ to the centroid frequency $\omega_c$ by a relationship $$\omega_v = \int_{\omega=0}^{\infty} (\omega-\omega_c)^2 P(\omega)d\omega \Big/ \int_{\omega=0}^{\infty} P(\omega)d\omega.$$

In one embodiment, the signal trace characteristic further includes a root-mean-square frequency $\omega_{RMS}$ by a relationship $$\omega_{RMS} = sqrt\left[\int_{\omega=0}^{\infty} \omega^2 P(\omega)d\omega \Big/ \int_{\omega=0}^{\infty} P(\omega)d\omega\right].$$

In one embodiment where the tissue attribute includes the spatial characteristic, the spatial characteristic includes information about propagation number k associated with the received acoustic energy. In one embodiment, the spatial characteristic further includes a longitudinal component $k_z=(\omega/v)\cos\theta$ and a transverse component $k_t=(\omega/v)\sin\theta$ of the propagation number k, where $\theta$ represents the arrival angle associated with the received acoustic energy.

In one embodiment, the spatial characteristic further includes a time gradient dt/dx along a selected transverse direction x. In one embodiment, the time gradient dt/dx is proportional to $\sin\theta/v$. In one embodiment, the time gradient dt/dx is proportional to $k_x/\omega$, where $\omega$ represents the frequency associated with the received acoustic energy. In one embodiment, the frequency $\omega$ is estimated by a centroid frequency $\omega_c$ associated with the received acoustic energy. In one embodiment, the frequency $\omega$ is estimated by an autocorrelation function A(t) associated with the received acoustic energy, evaluated at one time lag, so that $\omega=\arg|A(1)|$.

In one embodiment, the spatial characteristic further includes a time gradient dt/dy along a selected transverse direction y that is substantially perpendicular to the direction x. In one embodiment, the spatial characteristic further includes an azimuthal time gradient expressed as $\Delta\Phi=\arctan(dt/dy, dt/dx)$. In one embodiment, the spatial characteristic further includes a transverse time gradient expressed as $\Delta T=sqrt[(dt/dx)^2+(dt/dy)^2]$. In one embodiment, the spatial characteristic further includes a lateral continuity estimated as $\Delta^2 T=sqrt[(d^2t/dx^2)^2+(d^2t/dy^2)^2]$.

In one embodiment, the computer-executable instruction is further configured so as to perform the processing of the electrical signal at one or more ranges of frequency associated the electrical signal. In one embodiment, processing at the plurality of ranges of frequency includes a spectral decomposition analysis.

In one embodiment, the computer-executable instruction is further configured so as to classify the attribute based on its value. In one embodiment, the computer-executable instruction is further configured so as to generate a result value based on the classifying of the attribute. In one embodiment, the classifying of the attribute and the generating of the result are performed substantially automatically.

The foregoing features with respect to the animal tissue can also be applied to materials, where another embodiment of the present teachings relates to a computer-readable medium having a computer-executable instruction that is configured to process a signal so as to generate values of at least two attributes of a material, with the at least two attributes being selected from the group consisting of an amplitude-variations-with-offset characteristic, a signal trace characteristic, a spatial characteristic, and a spectral decomposition characteristic. The signal is based on an acoustic energy that has been reflected from the material.

BRIEF DESCRIPTION OF THE DRAWINGS

FIG. 1 shows one embodiment of an ultrasound system that transmits acoustic energy and detects scattered energy so as to determine a plurality of attributes associated with an object that scattered the acoustic energy;

FIG. 2 shows one embodiment of a process that can be performed by the ultrasound system of FIG. 1;

FIG. 11 shows that in one embodiment, scattered signal from an object can be received by a plurality of receivers and combined so as to generate an output having improved resolution and/or signal-to-noise ratio;

FIG. 12 shows one embodiment of a process that can achieve the functionality of the embodiment of FIG. 11;

These and other aspects, advantages, and novel features of the present teachings will become apparent upon reading the following detailed description and upon reference to the accompanying drawings. In the drawings, similar elements have similar reference numerals.

DETAILED DESCRIPTION OF SOME EMBODIMENTS

Figure 3A:
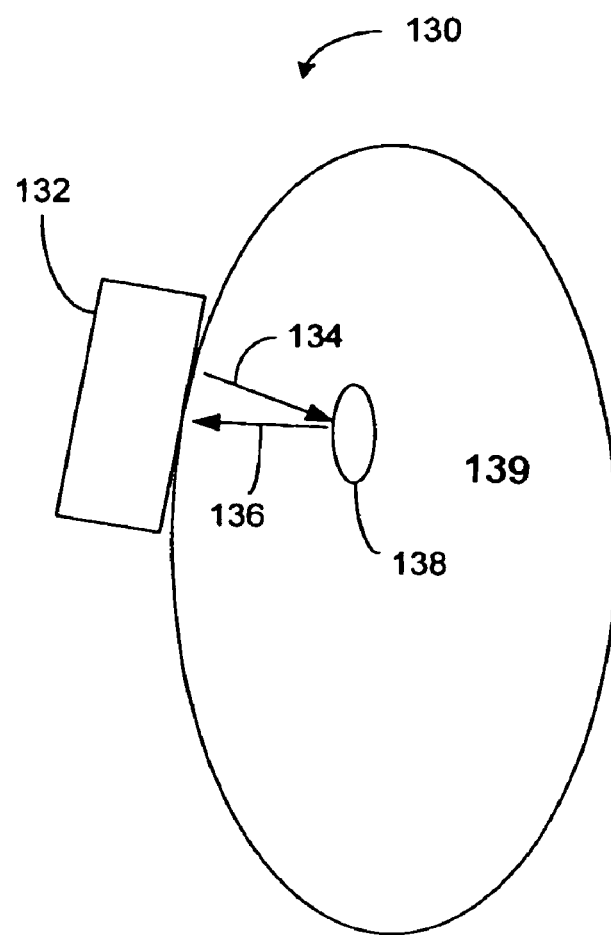
FIG. 3A shows that in one embodiment, the ultrasound system of FIG. 1 can be used in non-seismic applications such as tissue characterization.

The present teachings generally relate to systems and methods for using ultrasound to determine a plurality of attributes associated with an object in a medium. Such techniques have been used in seismic application to characterize underground features such as oil and mineral deposits. However, ultrasound techniques for determining attributes have not been used in non-seismic applications such as medical applications and materials testing applications. The present teachings address various techniques for attribute determination that could be used for medical or non-medical purposes. Materials application is an example of a non-medical use of the present teachings. Determining attributes of an animal tissue using acoustic energy can be either a medical or non-medical use. Non-medical uses can include, by way of examples, veterinary applications, post-mortem applications, and animal biopsy applications.

In conventional use, an ultrasound system is used to obtain an image or some form of a visual representation of an object in a medium. An image is typically formed by characterizing reflected signals from the medium by a plurality of picture elements (commonly referred to as "pixels"). Thus, a given pixel typically represents a given region of the medium. In the context of the present teachings, an image can be one of the attributes of the object. Other attributes may or may not have characteristics that can be represented in a "picture-like"

manner. Thus, for the purpose of describing a volume of a medium, the term "voxel" or "voxels" (volume element(s)) is used herein.

FIG. 1 shows an overview of one embodiment of an ultrasound system 100 that includes an acoustic device 102 that can be configured to transmit acoustic energy 108 into a medium 106 and detect scattered energy 110 therefrom. The scattered energy 110 can result from interaction of the acoustic energy 108 with an object 104 in the medium 106.

In one embodiment as shown in FIG. 1, the acoustic device 102 can be further configured to determine, or facilitate determination of, a plurality of attributes (indicated as a1, a2, ... ) associated with the object 104. Determination of such attributes can be based on the analysis of the scattered energy 110 in various manners described herein.

FIG. 2 shows one embodiment of a process 120 that can be performed by the ultrasound system 100 of FIG. 1. The process 120 begins at a start state 122, and in a process block 124, acoustic energy is transmitted to a selected location or region in a medium. In a process block 126, scattered acoustic energy is received from the medium. In a process block 128, a plurality of attributes associated with the selected location or region are determined based on the received energy. For the purpose of description, determining the plurality of attributes can include a mode of operation where the attributes are determined in some sequence, but not necessarily in parallel. The process 120 ends at a stop state 129.

FIG. 3A shows that in one example application 130, an ultrasound system 132 configured as described in FIGS. 1 and 2, can be used for attribute characterization of an object or region 138, such as tissue, that is part of a non-seismic medium 140. For the purpose of description, "seismic" means physical ground that forms the crust of the earth, but does not include bodies of water such as oceans, rivers, and lakes. Thus, the medium 140 can be part of a human being, anything that simulates a human being (e.g., cadaver, test medium, phantoms, and the like), and any living thing and simulation thereof. The medium 140 can also be a non-seismic structure such as a human-made structure.

In one embodiment as further shown in FIG. 3A, the ultrasound system 132 can be configured to transmit acoustic energy 134 into the non-seismic medium 139 and detect scattered energy 136. The system 132 can then analyze the scattered energy to determine a plurality of attributes as described herein.

Figure 3B:
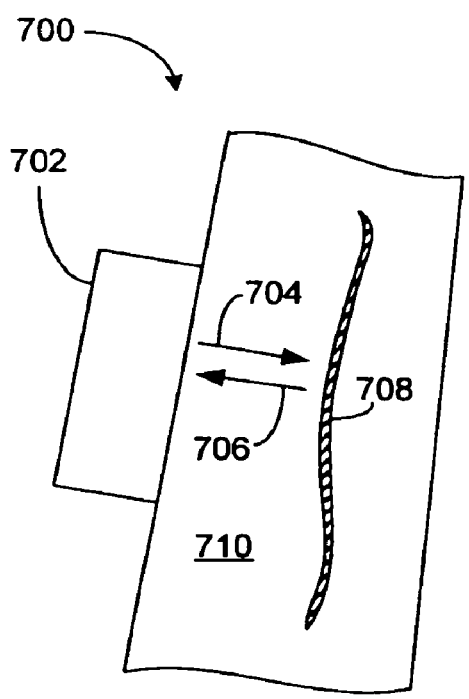
FIG. 3B shows that in one embodiment, the ultrasound system of FIG. 1 can be used in non-seismic applications such as non-destructive material characterization.

FIG. 3B shows that in one example application 700, an ultrasound system 702 configured as described in FIGS. 1 and 2, can be used for attribute characterization of an object or region 708 in a material 710 as part of non-destructive material testing.

In one embodiment as further shown in FIG. 3B, the ultrasound system 702 can be configured to transmit acoustic energy 704 into the material 710 and detect scattered energy 706 that results from the interaction of the acoustic energy 704 with features 708 such as cracks or voids. The system 702 can then analyze the scattered energy to determine a plurality of attributes as described herein.

The foregoing non-destructive testing method can be used to detect and/or characterize discontinuities, such as cracks and voids, within a given material. The non-destructive testing method can also be used to characterize various physical and mechanical properties, such as acoustic reflectivity and elastic modulus. As described herein, the non-destructive testing method can include characterization of various attributes based on the detection of acoustic signal.

It will be understood that non-destructive testing can include testing configurations where the material being tested is not deformed. In some material testing applications, a test material can be deformed but not destroyed. Such deformation can yield information about mechanical properties. With the various embodiments of the present teachings, a test material does not need to be deformed to yield various attributes, including one or more mechanical properties.

Figure 4:
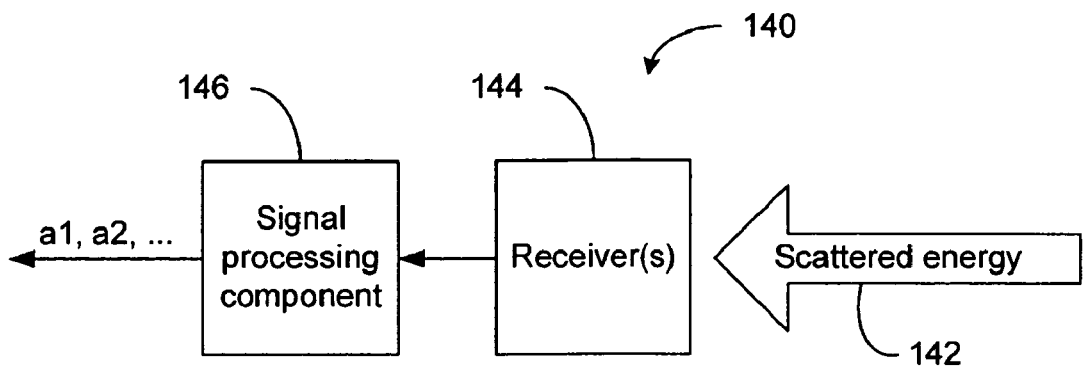
FIG. 4 shows a functional block diagram of one embodiment of the ultrasound system.

FIG. 4 shows a block diagram of one embodiment of an ultrasound system 140 that detects scattered energy 142 and generates a plurality of attributes (a1, a2, ... ). For the purpose of description of FIG. 4, it will be assumed that the scattered energy 142 is from interaction of a transmitted acoustic energy (not shown) with an object (not shown). The scattered energy 142 is shown to be detected by a receiver component 144 having one or more receivers. The receiver component 144 is shown to provide a signal to a processing component 146 that processes the signal to generate the plurality of attributes.

For the purpose of description herein, "processing component" may also be referred to simply as a "processor." It will be understood that "processing component" or "processor" can be a single component, but does not necessarily need to be a single component.

In general, it will be understood that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes, methods, functions, attributes, procedures, subroutines, segments of program code, drivers, firmware, microcode, circuitry, data, databases, data structures, tables, arrays, and variables.

Figure 5:
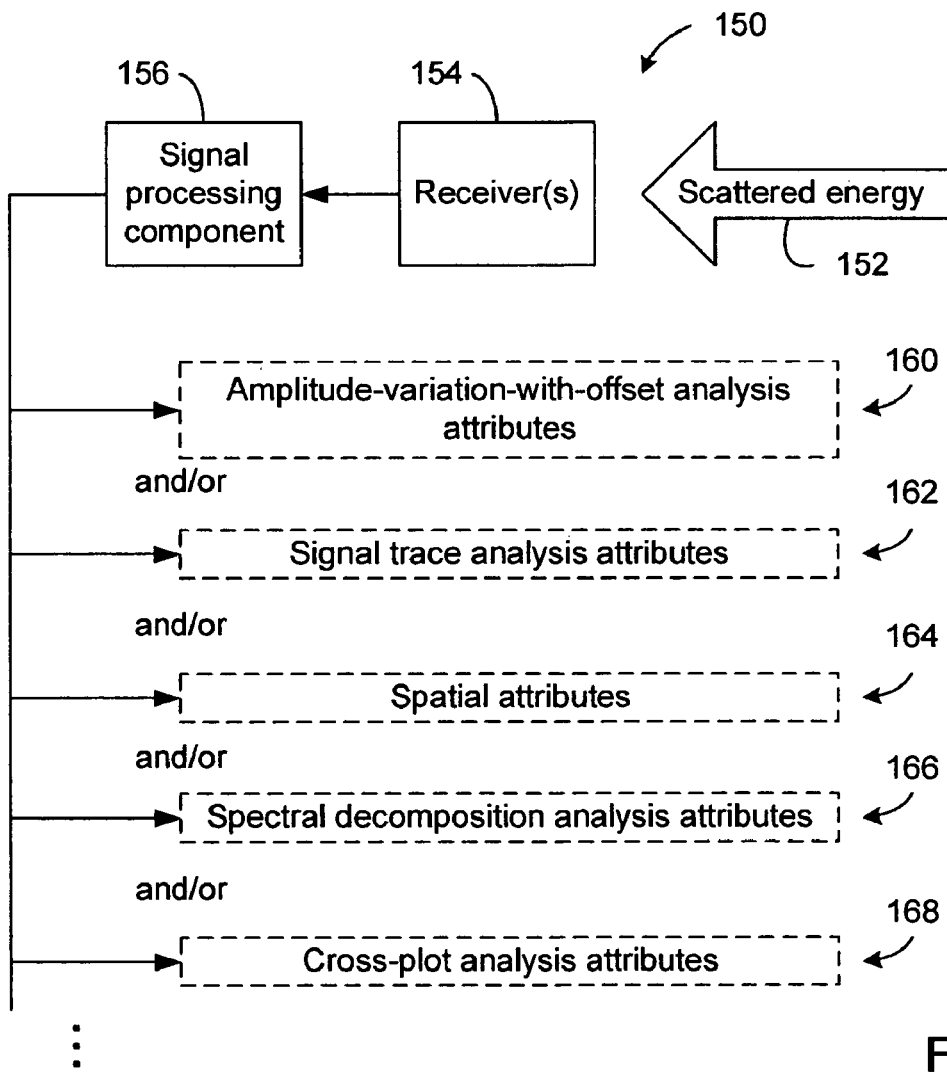
FIG. 5 shows example types of attributes that can be determined by the ultrasound system.

FIG. 5 shows one embodiment of an ultrasound system 150 that can be configured to determine different types of attributes based on detection and analysis of scattered energy 152 (again, transmitted energy and object not shown). The scattered energy 152 is shown to be detected by a receiver component 154, and the receiver component 154 is shown to provide a signal to a processor 156.

In one embodiment as shown in FIG. 5, the processor 156 can be configured to generate or facilitate generation of different types of attributes, including but not limited to attributes based on angular dependence analysis (160), attributes based on signal trace analysis (162), spatial attributes (164), attributes based on spectral analysis (166), and/or attributes based on cross-plot analysis (168). It should be understood that the foregoing example categorization is for the purpose of description, and is not intended to infer that a given attribute has to belong to one of the foregoing categories. Some attributes may be a result of two or more analyses. It should also be understood that the foregoing example attributes can be used with or without image-based attributes that are obtained either by the same system or separately.

FIGS. 6-12 show various example embodiments of a system and method for obtaining attributes based on angular dependence of the reflection of the acoustic energy. In some application, the angular-dependence analysis is often referred to as an amplitude-variations-with-offset (AVO) analysis. For the purpose of description, "AVO" analysis and angular-dependence analysis may be used interchangeably. It will be understood, however, that the use of the term AVO is not intended to preclude angular dependence analysis of quantities other than amplitudes.

Figure 6:
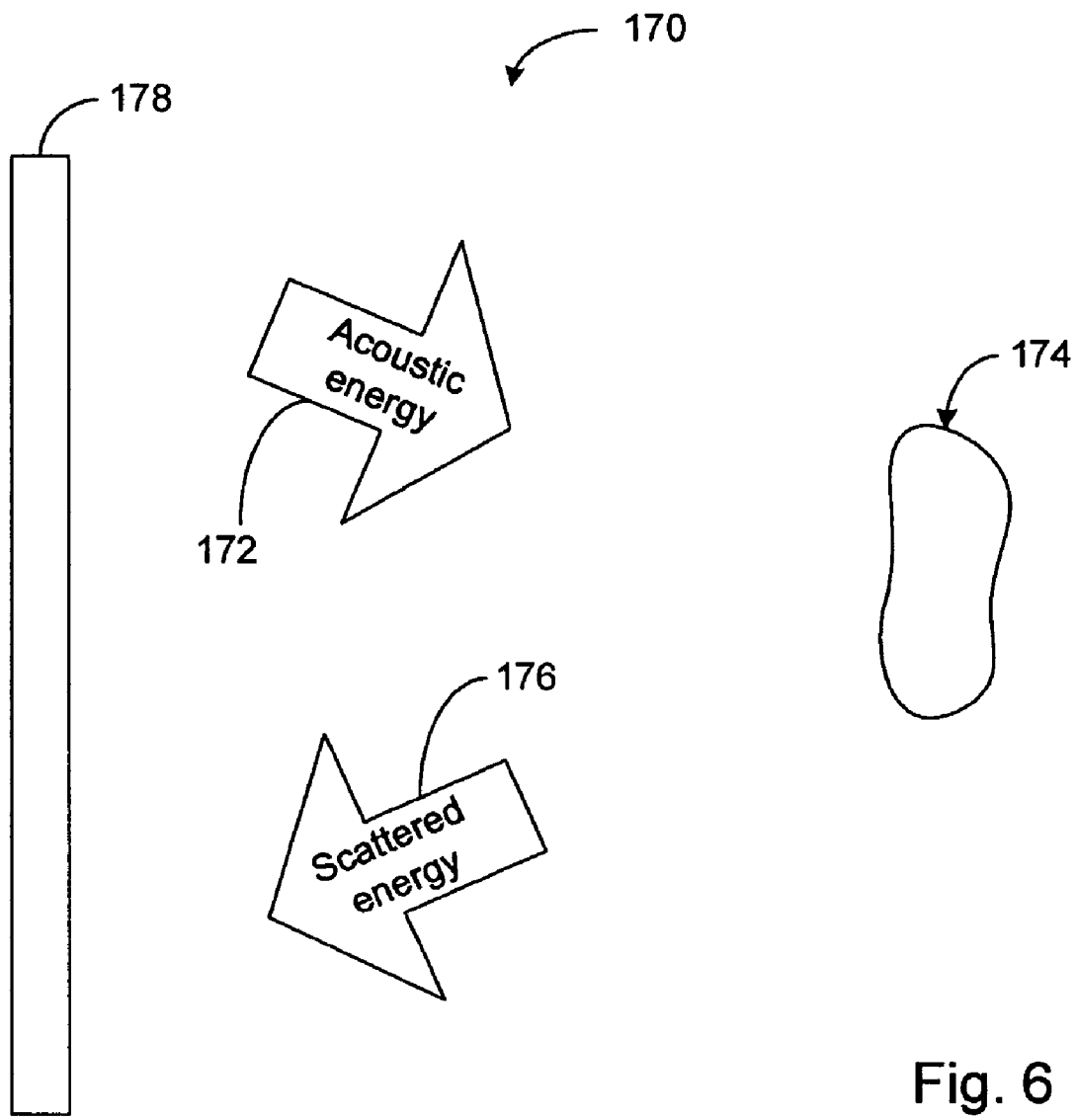
FIG. 6 shows that in one embodiment, the ultrasound system can be configured so as to allow determination of one of the types of attributes of FIG. 5—one or more attributes having angular dependencies.

In an example application 170 shown in FIG. 6, one embodiment of an ultrasound system 178 can be configured to transmit acoustic energy 172 to an object 174 in a medium, and to detect scattered energy 176 from the object 174. In one embodiment, the transmitted acoustic energy 172 is not focused, and the arrow 172 is depicted as pointing to the object 174 simply to indicate that at least some of the acoustic energy 172 reaches the object 174. Similarly, the scattered energy 176 does not need to be preferentially directed to any portion of the ultrasound system 178.

In one embodiment, the ultrasound system 178 can be configured to allow introduction of at least some angular variations in the directions of propagation of the acoustic energy 172 and the scattered energy 176, including the "directions" of the example "non-directional" acoustic energies described above. In one embodiment, such variations in the "directionality" can be achieved by varying the relative locations of the transmission of the acoustic energy 172 and the reception of the scattered energy 176 with respect to the object 174.

Figure 7:
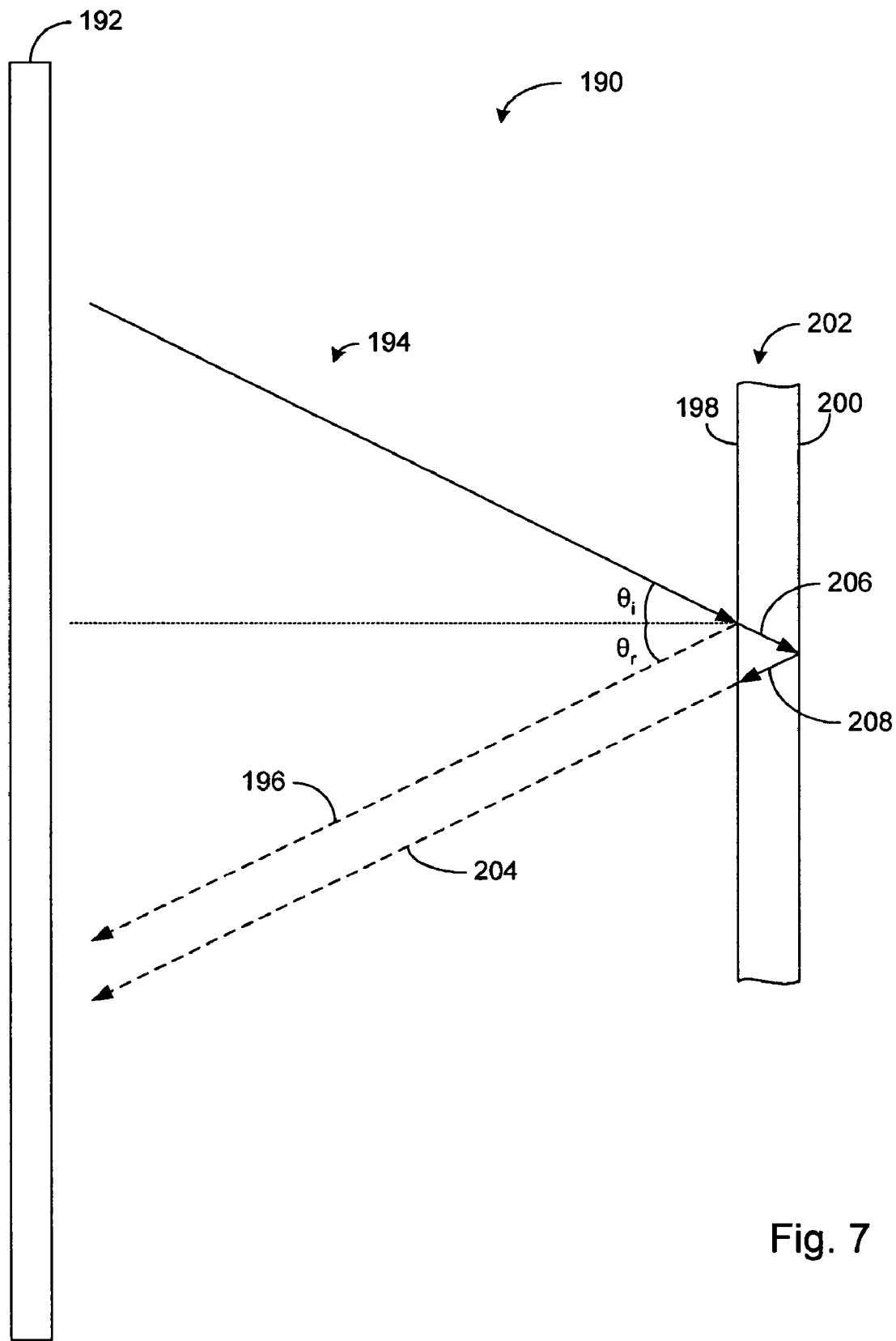
FIG. 7 shows an example of how the angle-dependent attributes can facilitate characterization of a layer of material in a medium.

FIG. 7 shows an example application 190, where one embodiment of an ultrasound system 192 is shown to transmit acoustic energy 194 (depicted as an arrow for the purpose of describing reflection) from a selected location of the system 192 towards an example object 202. The example object 202 can define one or more interfaces that reflect at least a portion of the acoustic energy 194. For example, the object 202 can include first and second interfaces 198, 200 that define the object 202 in the medium such as a tissue. Such interfaces can result in at least a portion of the acoustic energy 194 being reflected at the interfaces 198, 200. For example, a portion of the acoustic energy 194 can be reflected at the first interface 198 so as to yield a first reflected energy 196. A portion of the acoustic energy 194 can be transmitted through the object 202 (as acoustic energy 206) and impinge on the second interface 200. A portion of the impinging acoustic energy 206 can be reflected at the second surface 200 so as yield a reflected energy 208 that can eventually result in a second reflected energy 204.

In the particular example application 190 shown in FIG. 7, the detector surface is depicted as being generally parallel to the reflecting interfaces, and the reflections therefrom are depicted as being specular. That is, the angle of incidence $\theta_i$ is substantially equal to the angle of reflection $\theta_r$. For the purpose of description, $\theta_i$ and $\theta_r$ are measured relative to a line that is normal to the reflecting interface. Because of the specular nature of reflection, $\theta_i$ and $\theta_r$ may be simply referred to as reflection angle $\theta$.

As described herein, the reflection angle can be used as a variable in determining one or more attributes of the object where the reflection of the acoustic energy is occurring. Variation(s) in such attribute(s) with respect to the reflection angle can also yield additional attributes. Thus, the example reflection of the acoustic energy 194 at the first reflection interface 198 can provide information about the property of the object 202 with respect to the incident medium. Also, the example reflection of the impingin acoustic energy 206 at the second reflection interface 200 can provide information about the property of the object 202 with respect to the medium beyond the interface 200.

Figure 8:
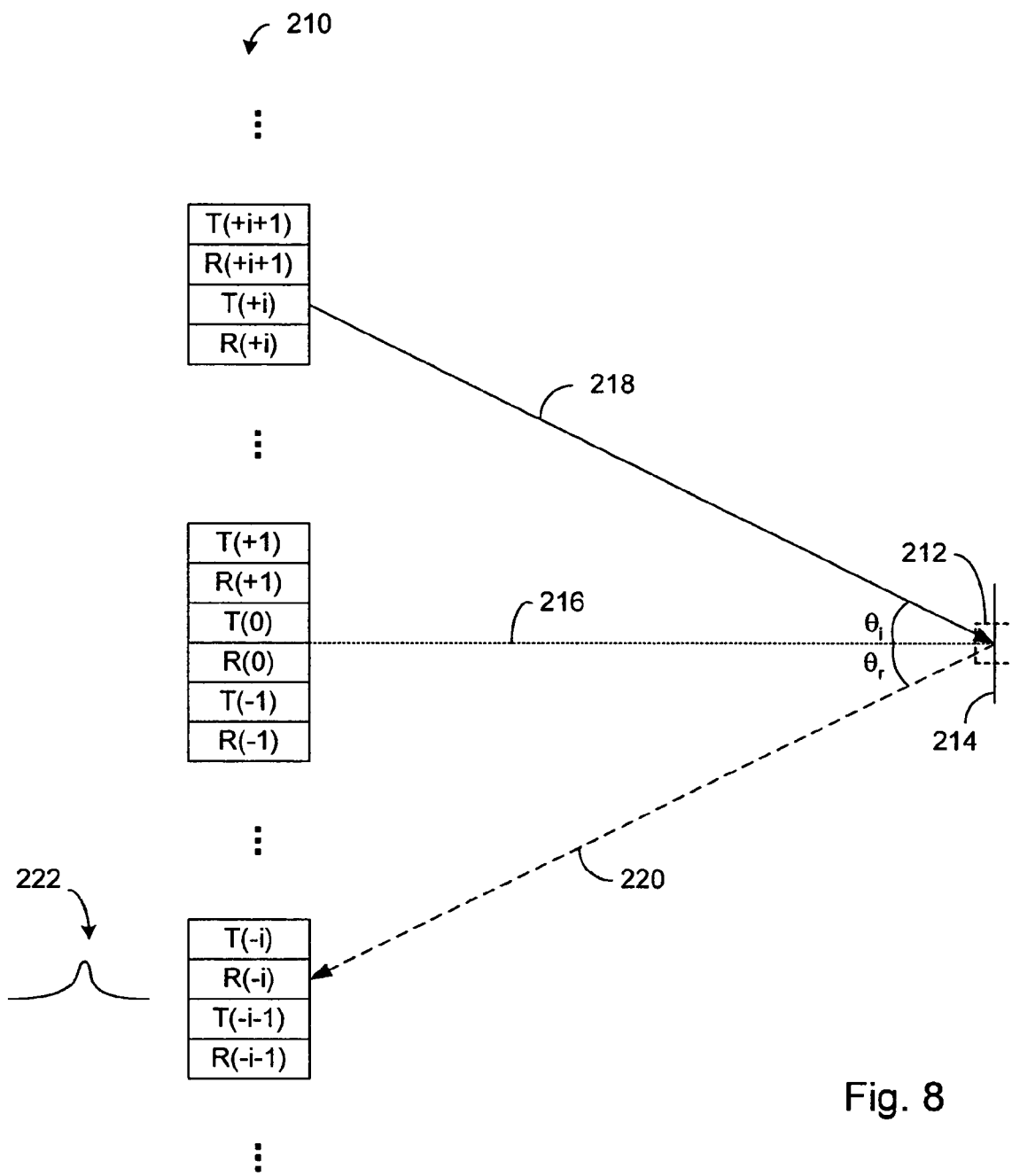
FIG. 8 shows one embodiment of the ultrasound system that can perform determination of the angle-dependent attributes of FIG. 7.

FIG. 8 shows one embodiment of a detector assembly 210 that can be configured to provide the reflection angle dependence analysis capability of an ultrasound system. As shown, the detector assembly 210 can include an array of transmitters (T) and receivers (R) that are positioned relative to each other in some known manner. Such an array can be used to analyze the reflective property of an interface 214 in or about a selected volume element (voxel) 212.

Thus, with respect to the example voxel 212, a normal line 216 can provide a reference for determining the reflection angle $\theta$. That is, the positions of transmitters and receivers with respect to such a reference can provide information about the reflection angle $\theta$. For example, an example acoustic energy 218 transmitted from the transmitter T(i) is shown to reflect from the example voxel 212, such that a reflected energy 220 is detected by the receiver R(−i). The receiver R(−i) is shown to generate an electrical signal 222 that can be processed to provide information about the reflection in a manner described below in greater detail.

As shown in FIG. 8, different data sets at different reflection angles can be obtained. For example, a larger angle data set can be obtained for the example voxel 212 by transmitting from transmitter T(i+1) and receiving by receiver R(−i−1).

It will be understood that, in FIG. 8, the numbering scheme for the transmitters and receivers (being generally symmetrical with respect to the example voxel 212) is for the purpose of description. The transmitters and receivers can be indexed in any manner; and thus the indexing example in FIG. 8 is not a requirement.

Similar to the example application described above in reference to FIG. 7, the particular example of FIG. 8 depicts the detector surface as being generally parallel to the reflecting interface. For the purpose of analyzing the reflection angle dependence of attribute(s), however, such assumption is not necessary.

Figure 9:
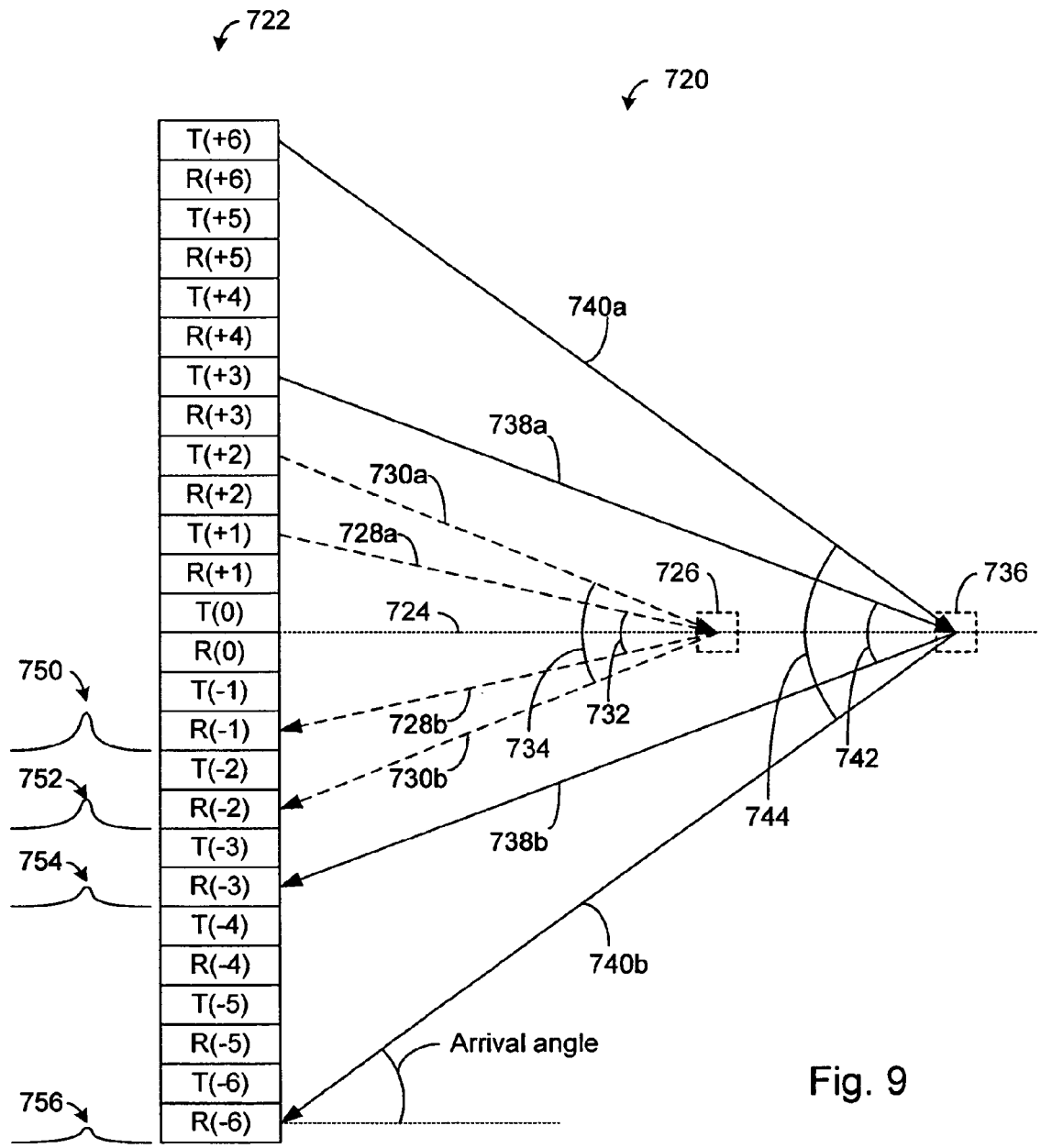
FIG. 9 shows an example of how reflection angles can be estimated with respect to a given location in a medium.

FIG. 9 shows an example application 720 where reflection angles can be estimated based on some symmetry of a detector assembly 722 with respect to one or more selected voxels 726, 736. The detector assembly 722 is depicted as having an array of transmitters and receivers numbered symmetrically about a mid-line 724. Of course, such numbering (symmetric or not) is not necessary, and is only used for the purpose of description.

The two example voxels 726 and 736 are shown to be along the mid-line 724. For a given voxel, transmission and reception from generally symmetric pair of transmitter and receiver can be used to estimate the reflection geometry, and therefore estimate the reflection angle for a feature located at or about the given voxel.

For example, two reflection geometries are shown for the example voxel 726. A first transmitted acoustic energy from transmitter T(+1) is depicted as an arrow 728a, and a reflection of that energy from the voxel 726 is depicted as an arrow 728b. The reflection 728b is depicted as being received by receiver R(−1) so as to yield a signal 750. For the signal 750, the reflection angle can be estimated as being half of an opening angle 732 defined by the arrows 728a and 728b about the voxel 726. The opening angle 732 or the corresponding reflection angle can be estimated based on the reflection geometry. For example, knowledge of the distances of T(+1) and R(−1) with respect to the mid-line 724 and the distance between the detector array 722 and the voxel 726 can be used to calculate the reflection angle. If the propagation distances (lengths of arrows 728a and 728b) are needed, they can be estimated by multiplying the propagation time and an estimate of propagation velocity. Each of the transmission distance (728a) and the reflection distance (728b) can then be estimated as being approximately half of that distance.

As further shown in FIG. 9, other reflection angle data can be obtained for the example voxel 726. For example, transmission 730a from transmitter T(+2) and reflection 730b to receiver R(−2) can yield another reflection geometry, corresponding opening angle 734, and a signal 752 with respect to the voxel 726.

As further shown in FIG. 9, similar reflection angle data can be obtained for other voxels along the example mid-line 724. For example, transmission 738a from transmitter T(+3) and reflection 738b to receiver R(−3) can yield a reflection geometry, corresponding opening angle 742, and a corresponding signal 754 with respect to the voxel 736. Similarly, transmission 740a from transmitter T(+6) and reflection 740b to receiver R(−6) can yield another reflection geometry, corresponding opening angle 744, and a corresponding signal 756 with respect to the voxel 736.

Figure 10:
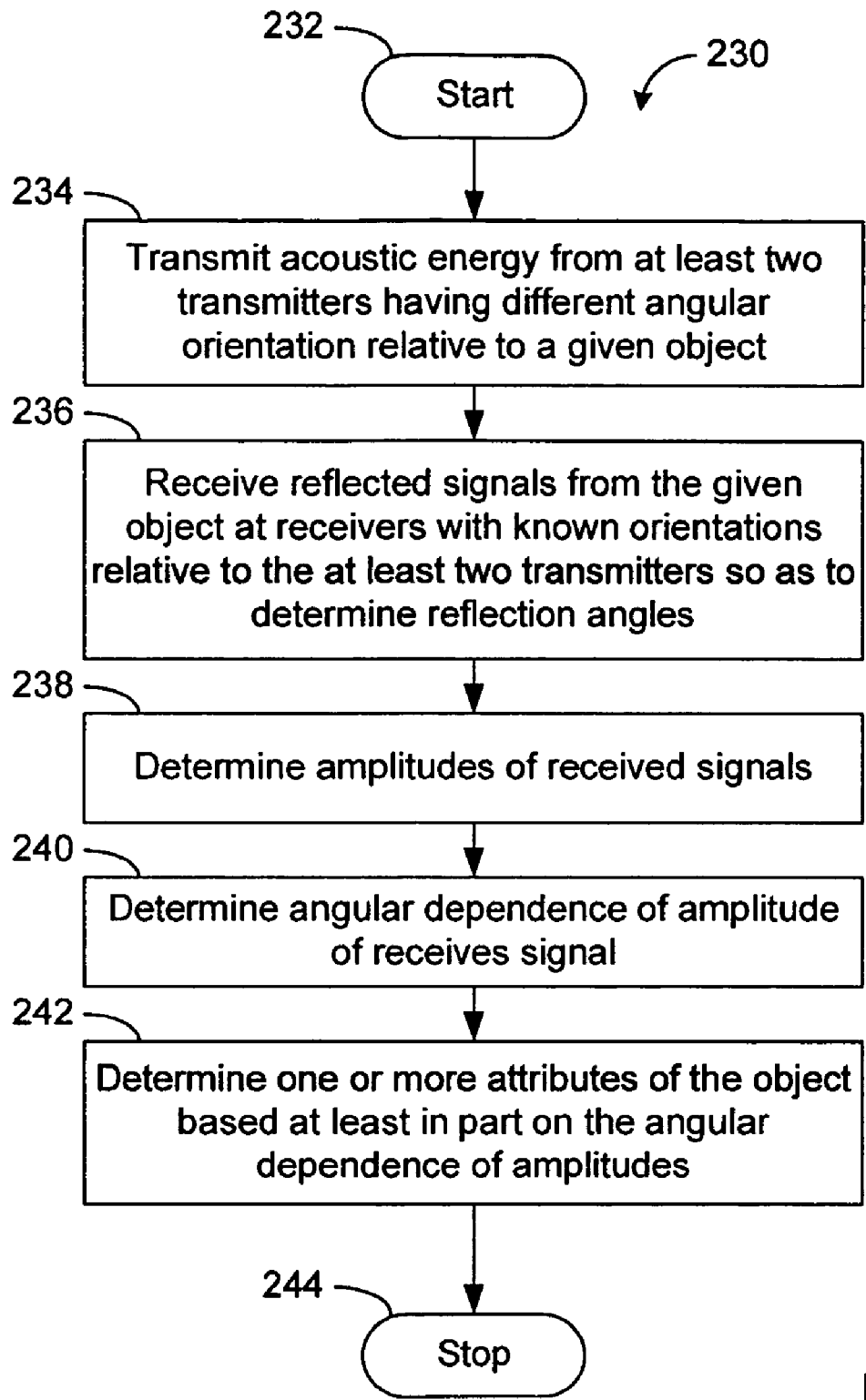
FIG. 10 shows one embodiment of a process that can achieve the angular dependency determination of FIG. 8.

FIG. 10 shows one embodiment of a process 230 that can be implemented with the various embodiments of the ultrasound system described above in reference to FIGS. 6-8. The process 230 begins at a start state 232, and in a process block 234, acoustic energy is transmitted from at least two transmitters having different angular orientation with respect to an object in a medium. In one embodiment, such transmissions are performed in sequence. In a process block 236, reflected signals are received from the object by receivers that are positioned at known orientations relative the at least two transmitters, to receive reflections from the object. The relative orientation of the transmitters and receivers with respect to the object allows determination of reflection angles in a manner, for example, described above in reference to FIG. 9.

As further shown in FIG. 10, the process 230 in a process block 238 determines one or more properties of the received signals. In one embodiment, amplitudes of the received signals are determined. In a process block 240, angular dependence of the amplitudes is determined. In a process block 242, one or more attributes of the object are determined, based at least in part on the angular dependence of the amplitudes. The process 230 ends at a stop state 244.

An example angular-dependence analysis is now described. As described in greater detail, such analysis can yield attributes that can be used as estimates of certain mechanical properties of an object in the medium.

In one embodiment, the angular-dependence analysis includes an amplitude-variation-with-offset (AVO) analysis. In one embodiment of the AVO method, a reflection amplitude R is sometimes expressed as an equation known as the Shuey three-term approximation to the Zoeppritz equation $$R(\theta)=A+B\sin^2\theta+C\sin^2\theta\tan^2\theta \qquad (1)$$

where θ represents the reflection angle, and coefficients A, B, and C are constants. Additional details about Equation 1 can be found in various literatures (for example, in an article by Shuey, R. T., "A simplification of the Zoeppritz equations," *Geophysics*, 50, 609-614, 1985). By obtaining a plurality of reflection amplitudes of signals from the receivers at different angles, example Equation 1 can be fit by, for example, one of known numerical techniques to obtain estimates for the coefficients A, B, and C. The coefficient A is commonly referred to as an AVO intercept; B is commonly referred to as an AVO gradient; and C is commonly referred to as an AVO curvature.

In one embodiment, the quantities R, A, B, and C can be considered to be attributes associated with the object where the reflections occurred. As described below, estimates of mechanical properties can be obtained from the combination of some of these quantities.

In certain applications, the third term of Equation 1 can be dropped (for example, when the reflection angles are relatively small, less than about 30 degrees), and the reflection amplitude can be estimated as $$R(\theta)=A+B\sin^2\theta. \qquad (3)$$

With such an estimate, a linearized relationship between R and $\sin^2\theta$ can be fit with a linear line to obtain an intercept A and a slope B. Such a simplified equation can provide a relatively easier determination of the coefficients A and B.

In certain applications, an assumption can be made, where for example $V_P/V_S=2$ (that is, the compressional velocity is approximately twice that of the shear velocity). Then, it can be shown that estimates of zero-offset reflectivity parameters $R_{P0}$ and $R_{S0}$ can be obtained and expressed as $R_{P0}=A$; $R_{S0}=(A-B)/2$.

In certain applications such as animal tissue characterization, an assumption can be made, where $V_P/V_S=3$. Then, it can be shown that estimates of zero-offset reflectivity parameters $R_{P0}$ and $R_{S0}$ can be obtained and expressed as $R_{P0}=A$; $R_{S0}=(4A-9B+5C)/8$. The parameters A, B, and C can be estimated using Equation 1 (for example, by curve-fitting), provided sufficiently long offsets are available. Otherwise, A and B can be estimated from Equation 2, while C can be estimated from a velocity model where C can be given as approximately half of the ratio of the velocity contrast to the average velocity across the reflecting interface.

These zero-offset reflectivity parameters can further be inverted using a known technique (such as is described in a paper by Russell, B., and Hampson, D., 1991, "A comparison of post-stack seismic inversion techniques": 61st Ann. Internat. Mtg., Soc. Expl. Geophys., Expanded Abstracts, 876-878) to obtain estimated values of compressional impedance $Z_P$ and shear impedance $Z_S$. The impedance parameters $Z_P$ and $Z_S$, defined as $Z_P=\rho V_P$ and $Z_S=V_S$ (ρ being the density), can be used to obtain other attributes as described below.

In certain applications, values of one or more elastic properties (example attributes) of the object can be estimated based on the compressional and shear impedance values $Z_P$ and $Z_S$. As an example, a rigidity parameter μ, that corresponds to resistance to shear deformation, can be estimated by a relationship $\mu=Z_S^2/\rho$, where ρ represents an estimate of the density of the reflecting object. In another example, an elastic parameter λ, that is sensitive to fluid content of the reflecting object, can be estimated by a relationship $\lambda=(Z_P^2-2Z_S^2)/\rho$. In yet another example, a parameter κ, that corresponds to incompressibility or bulk modulus of the reflecting object, can be estimated by a relationship $\kappa=\lambda+(2/3)\mu$.

FIG. 11 shows one embodiment of an ultrasound system 270 that is analyzing a reflecting feature 276 in or about a given voxel 274 with example midline 278. An acoustic energy 280 is shown to be transmitted from a transmitter 272, and incident on the reflecting feature 276. In some situations, the reflecting feature 276 may not provide an ideal reflecting surface; and the resulting scattered energy 286 may reach a plurality of receivers 288. An angle of incidence 282 is shown to be generally the same as an average reflection angle 284, with the average being determined by the orientations of the plurality of receivers 288 that receive the scattered energy 286.

As further shown in FIG. 11, signals received by the plurality of receivers 288 can be combined to yield a combined signal. Such combination can be achieved, for example, by a technique disclosed in a co-pending patent application (U.S. patent publication no. US 2006/0064015, and entitled "SYSTEMS AND METHODS FOR IMPROVED IMAGING").

FIG. 12 shows one embodiment of a process 290 that can be implemented to achieve the combining of the reflected signals as described above in reference to FIG. 11. In a process block 292, acoustic energy is transmitted from a selected transmitter. In a process block 294, scattered energy is received by a plurality of receivers, whose average angular orientation corresponds to a substantially specular reflection with respect to the selected transmitter. In a process block 296, the received signals can be combined to obtain a reflection amplitude at the average angular orientation.

Figure 13:
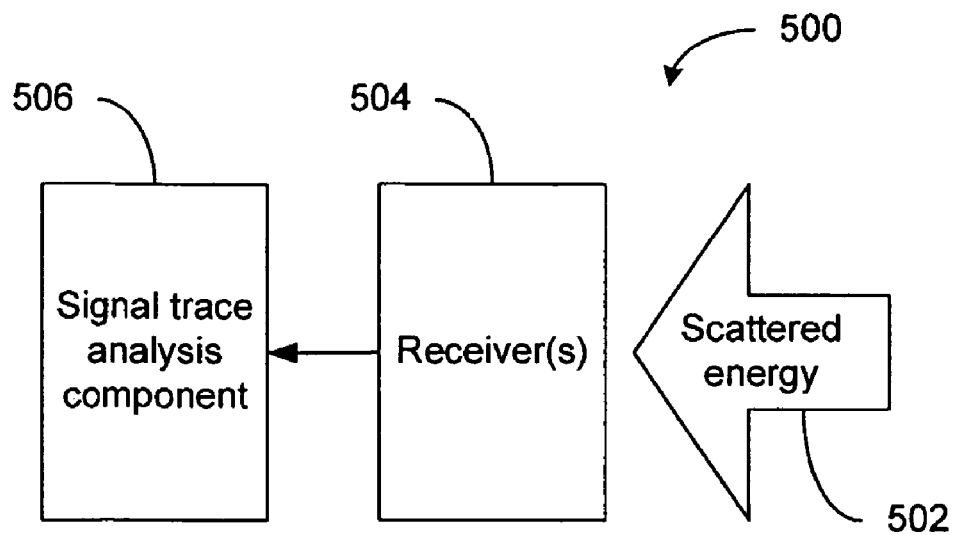
FIG. 13 shows that in one embodiment, the ultrasound system can be configured so as to allow determination of another one of the types of attributes of FIG. 5—one or more attributes based on trace analysis.

FIG. 13 now shows a block diagram of one embodiment of an ultrasound system 500 having a receiver component 504 that receives scattered energy 502. The receiver component 504 can have one or more receivers.

As further shown in FIG. 13, the ultrasound system 500 also includes a component 506 that can be configured to perform signal trace analysis on one or more electrical signals obtained from the receiver component 504.

In one embodiment, the signal trace analysis can be based on performing some form of a transformation of a measured electrical signal, and combining the result with the un-transformed signal to characterize the signal. As an example, if the electrical signal from the receiver (as a result of detecting reflected energy from the reflecting object) can be expressed as a time-varying function f(t), a Hilbert transform can be performed on f(t) to yield g(t). The signal can then be characterized as a complex function F(t)=f(t)+ig(t), where f(t) represents the real part, and g(t) represents the imaginary part.

A number of operations can be performed on such an example signal-characterizing function. Such known operations can be found in various references, including for example, a paper by M. Turhan Taner, entitled "Attributes Revisited," 1992 (Revised 2000), and available from the website http://www.rocksolidimages.com/pdf/attrib_revisited.htm. Some notable operations are summarized as follows.

In one example, an attribute can be a modulus E(t) of the complex function F(t), expressed as $E(t)=(f^2(t)+g^2(t))^{1/2}$. In some applications, the function E(t) represents an envelope of the electrical signal generated by the receiver. In some applications, the function E(t) represents a value corresponding to a substantially instantaneous amplitude or reflection strength associated with the received acoustic energy.

In one example, an attribute can be a rate of change of the attribute E(t) with respect to time, expressed as d(E(t))/dt. In some applications, the attribute d(E(t))/dt can provide information about absorption effects in the reflecting object.

In one example, an attribute can be a rate of change of the attribute d(E(t))/dt, expressed as $d^2(E(t))/dt^2$. In some applications, the attribute $d^2(E(t))/dt^2$ can provide information about reflecting interfaces in or about the reflecting object.

In one example, a total instantaneous energy can be expressed as $E^2(t)$—that is, the square of the envelope E(t). An attribute can be a rate of change of the total energy with respect to time, expressed as $d(E^2(t))/dt=2E(t)d(E(t))/dt$, that can also provide information about absorption effects in the reflecting object. An attribute can be a second time derivative of the total energy, expressed as $d^2(E^{2(t)})/dt^2=2[d(E(t))/dt]^2+2[E(t)d^2(E(t))/dt^2]$, that can provide information about reflecting interfaces in or about the reflecting object.

In one example, an attribute can be a substantially instantaneous phase of the received acoustic energy from the reflecting object, expressed as $\Phi(t)=\arctan(g(t)/f(t))$. In some applications, the phase attribute $\Phi(t)$ can provide information about propagation phase of the acoustic energy from the reflecting object.

In one example, an attribute can be a substantially instantaneous frequency of the received acoustic energy from the reflecting object, expressed as $\omega(t)=d(\Phi(t))/dt$.

In one example, an attribute can be a substantially instantaneous acceleration of the received acoustic energy from the reflecting object, expressed as $a(t)=d\omega(t)/dt$.

In one example, an attribute can be a mean frequency $\omega_{mean}(t)$ of the received acoustic energy from the reflecting object. The mean frequency $\omega_{mean}(t)$ can be obtained by: (1) determining a Fourier transform $F(\omega)$ of the function F(t); (2) determining an autocorrelation function $P(\omega)$ by a relationship $P(\omega)=F(\omega)F^*(\omega)$, where $F^*(\omega)$ represents a complex conjugate of $F(\omega)$; (3) determining a normalized autocorrelation function A(t) by a relationship $$A(t) = \int_{\omega=0}^{\infty} P(\omega)\exp(i\omega t)d\omega \bigg/ \int_{\omega=0}^{\infty} P(\omega)d\omega;$$

and (4) determining the mean frequency $\omega_{mean}$ by a relationship $$\omega_{mean}(t) = dA(t)/dt = -i\int_{\omega=0}^{\infty} \omega P(\omega)\exp(i\omega t)d\omega \bigg/ \int_{\omega=0}^{\infty} P(\omega)d\omega.$$

In one example, the mean frequency $\omega_{mean}$ can also be determined by a relationship $$\omega_{mean}(t) = \int_{\omega=0}^{\infty} \omega P(\omega)LPF(t,\omega)d\omega \bigg/ \int_{\omega=0}^{\infty} P(\omega)d\omega,$$

represents a low pass filter that can be time-variant if desired.

In one example, an attribute can be a thin-layer indicator parameter that can be determined by a relationship $\omega(t)-\omega_{mean}(t)$.

In one example, an attribute can be an acceleration of the received acoustic energy from the reflecting object, expressed as $|d^2A(t)/dt^2|$.

In one example, an attribute can be a centroid frequency $\omega_c$ of a power spectrum, expressed as $$\omega_c = \int_{\omega=0}^{\infty} \omega P(\omega)d\omega \bigg/ \int_{\omega=0}^{\infty} P(\omega)d\omega.$$

In one example, an attribute can be a variance $\omega_v$ to the centroid frequency $\omega_c$, expressed as $$\omega_v = \int_{\omega=0}^{\infty} (\omega - \omega_c)^2 P(\omega)d\omega \bigg/ \int_{\omega=0}^{\infty} P(\omega)d\omega.$$

In one example, an attribute can be a root-mean-square frequency $\omega_{RMS}$, expressed as $$\omega_{RMS} = sqrt\left[\int_{\omega=0}^{\infty} \omega^2 P(\omega)d\omega \bigg/ \int_{\omega=0}^{\infty} P(\omega)d\omega\right].$$

Again, it should be understood that the foregoing example attributes are just that—examples. Thus, these examples should not be construed as limiting the scope of the present teachings.

Figure 14:
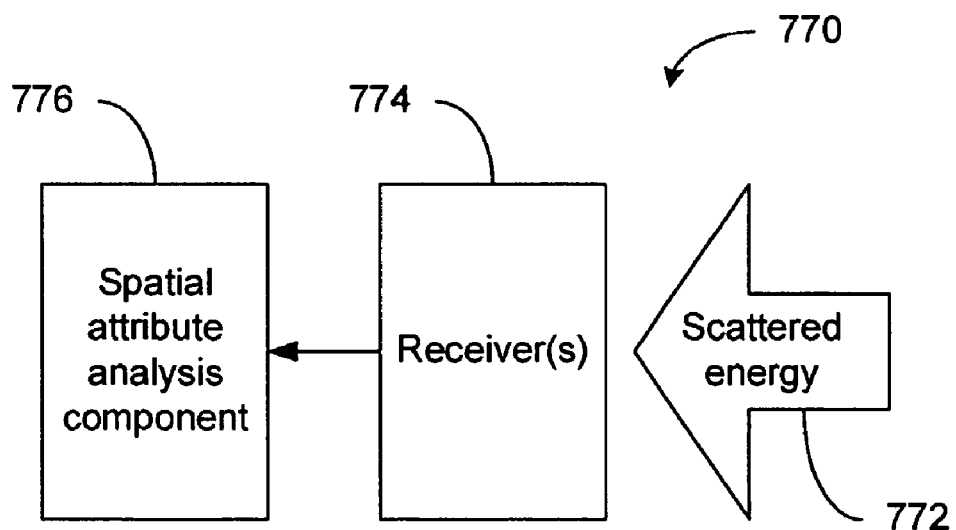
FIG. 14 shows that in one embodiment, the ultrasound system can be configured so as to allow determination of another one of the types of attributes of FIG. 5—one or more spatial attributes.

FIG. 14 now shows a block diagram of one embodiment of an ultrasound system 770 having a receiver component 774 that receives scattered energy 772. The receiver component 774 can have one or more receivers.

As further shown in FIG. 14, the ultrasound system 770 also includes a component 776 that can be configured to perform analysis of spatial attributes associated with one or more electrical signals obtained from the receiver component 774.

A number of operations can be performed to obtain spatial attributes. Such known operations can be found in various references, including for example, a paper by M. Turhan Taner, entitled "Attributes Revisited," 1992 (Revised 2000), and available from the website http://www.rocksolidimages.com/pdf/attrib_revisited.htm. Some notable operations are summarized as follows.

The example signal trace analysis described above in reference to FIG. 13 can provide, among others, temporal information about the various attributes. In one embodiment, spatial attributes include attributes having spatial information that extend from the temporal information. For example, propagation number k of the received signal can be obtained based on the frequency $\omega$ (which can be determined as described above in reference to FIG. 13) as k=$\omega$/v, where v is the propagation velocity of the reflected signal. If one defines z-direction as being along a line passing through the reflecting location and normal to the receiving detector, the longitudinal and transverse components of the propagation number k can be expressed as $k_z=(\omega/v)\cos\theta$, and $k_t=(\omega/v)\sin\theta$, where $\theta$ represents an arrival angle that can be defined as the angle between the arrival path and the line normal to the receiveing detector, and the subscript "t" indicates transverse direction which can be x, y, or some combination thereof. An example of an arrival angle is depicted in FIG. 9. In such example embodiments, the arrival angle is substantially equal to the reflection angle. However, for the purpose of spatial attribute analysis, such an assumption (the arrival angle being substantially equal to the reflection angle) is not a requirement.

One example spatial attribute is a time gradient dt/dx along the x-direction, that can be expressed as $\sin\theta/v$. Thus, dt/dx can also be expressed as $dt/dx=k_x/\omega$. In one embodiment, the instantaneous frequency $\omega$ can be approximated by the centroid frequency $\omega_c$ (described above in reference to FIG. 13). Alternatively, the instantaneous frequency $\omega$ can be estimated by evaluating the autocorrelation function A(t) at one time lag. That is, $\omega=\arg|A(1)|$.

In one embodiment, the propagation number $k_x$ can be estimated by evaluating the autocorrelation function A(t) at one time lag and calculated along the x-direction. That is, $k_x=\arg|A_x(1)|$.

In a similar manner, a time gradient dt/dy along the y-direction can be expressed as $dt/dy=k_y/\omega$, with $\omega=\arg|A(1)|$ and $k_y=\arg|A_y(1)|$. Also, a transverse time gradient can then be expressed as $\Delta T=\text{sqrt}[(dt/dx)^2+(dt/dy)^2]$, and an azimuthal time gradient can be expressed as $\Delta\Phi=\arctan(dt/dy, dt/dx)$. The attributes $\Delta T$ and $\Delta\Phi$ are sometimes referred to as instantaneous phase dip and instantaneous azimuthal dip.

Another example spatial attribute is lateral continuity of reflecting interfaces. In one embodiment, the lateral continuity can be estimated by obtaining another derivative of the phase dip $\Delta T$, such that $\Delta^2 T=\text{sqrt}[(d^2t/dx^2)^2+(d^2t/dy^2)^2]$.

The foregoing example spatial attributes can be used to obtain a plurality of other attributes. For example, lateral semblance attribute, and attributes related to such lateral semblance can be estimated.

Figure 15:
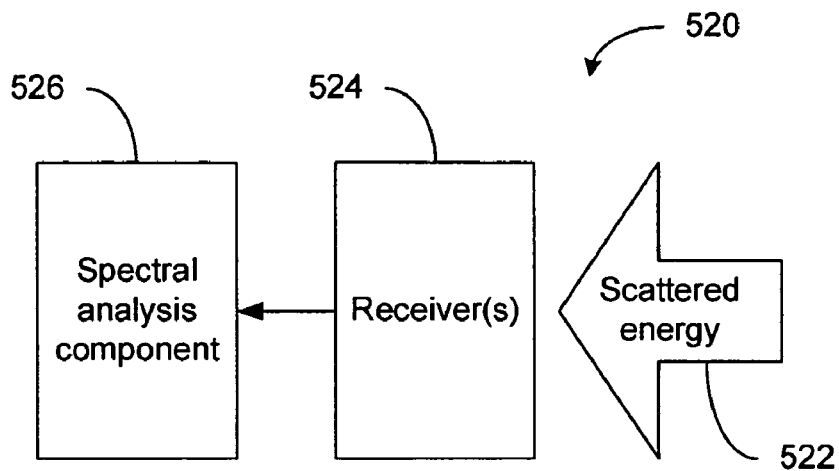
FIG. 15 shows that in one embodiment, the ultrasound system can be configured so as to allow determination of yet another one of the types of attributes of FIG. 5—one or more attributes based on spectral analysis.

FIG. 15 now shows a block diagram of one embodiment of an ultrasound system 520 having a receiver component 524 that receives scattered energy 522. The receiver component 524 can have one or more receivers.

As further shown in FIG. 15, the ultrasound system 520 also includes a component 526 that can be configured to perform spectral analysis on one or more electrical signals obtained from the receiver component 524. In one embodiment, the spectral analysis includes analysis of the one or more electrical signals at different frequency ranges. For example, at least some of the AVO-type analyses and/or signal trace-type analyses described above can be performed for different frequency ranges of the electrical signals obtained from the receiver component 524. Performing such a spectral analysis can reveal frequency dependence of some of the attributes thus obtained.

Figure 16A:
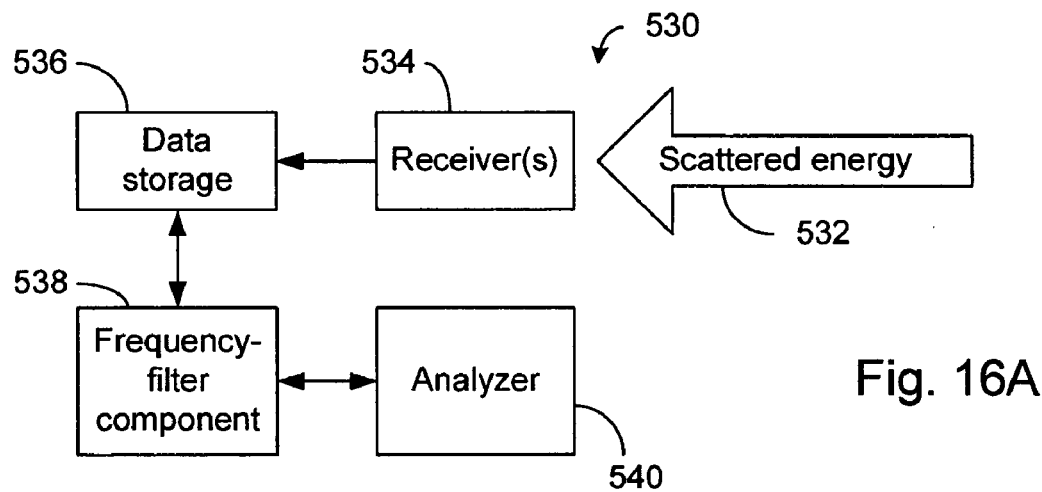
FIGS. 16A and 16B show example embodiments of the ultrasound system configured so as to perform the spectral analysis of FIG. 15.
Figure 16B:
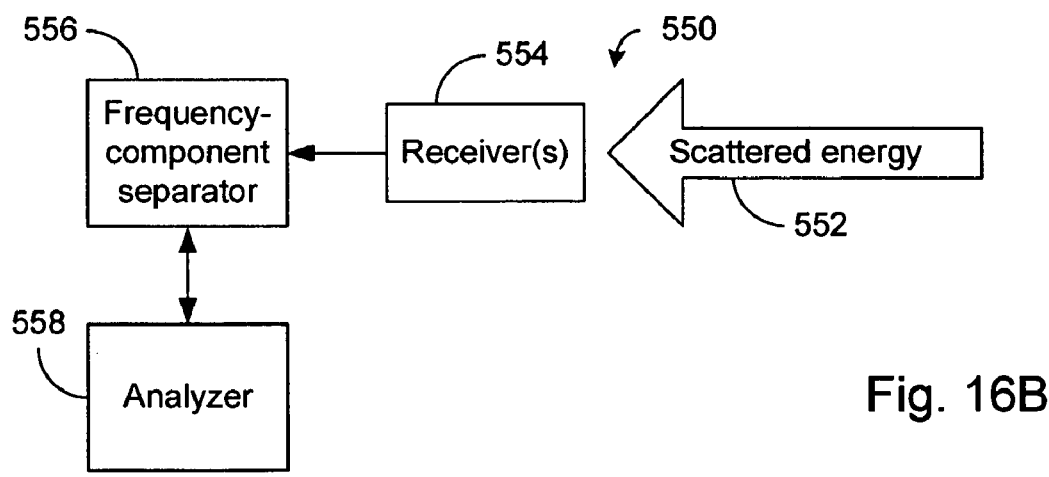

Electrical signals can be analyzed at different frequency ranges in various known techniques. FIGS. 16A and 16B show examples of how such analysis can be performed. In one embodiment as shown in FIG. 16A, an ultrasound system 530 can include a receiver component 534 that receives scattered energy 532 and outputs one or more raw electrical signals to a storage component 536. The system 530 can further include a filter component 538 that can be configured to retrieve and select a desired frequency band of the stored raw signal. Such filtered signal having the desired frequency band can then be analyzed by an analyzer component 540. In one embodiment, the analyzer component 540 can include any of the functionalities described herein (e.g., AVO analysis and/or signal trace analysis).

In one embodiment as shown in FIG. 16B, an ultrasound 550 can include a receiver component 554 that receives scattered energy 552 and outputs one or more raw electrical signals to a component 556 that can be configured to separate and generate one or more frequency bands of the raw electrical signals. Such frequency-separated signals can then be analyzed by an analyzer component 558. In one embodiment, the analyzer component 558 can include any of the functionalities described herein (e.g., AVO analysis and/or signal trace analysis).

Figure 17:
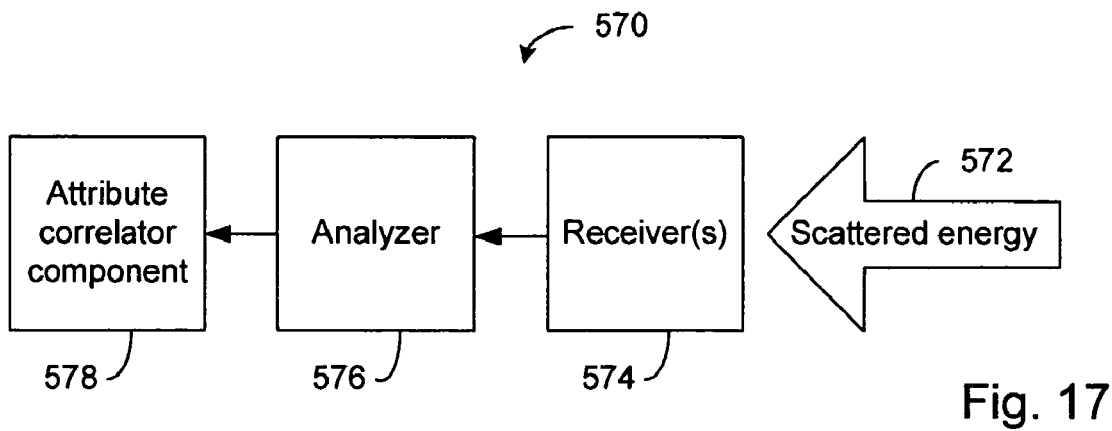
FIG. 17 shows that in one embodiment, the ultrasound system can include a component that presents one or more attributes or correlates different attributes so as to facilitate determination of additional information therefrom.

FIG. 17 now shows a block diagram of one embodiment of an ultrasound system 570 having a receiver component 574 that receives scattered energy 572. The receiver component 574 can have one or more receivers. The receiver component 574 can provide one or more electrical signals to an analyzer component 576. In one embodiment, the analyzer component 576 can include any of the functionalities described herein (e.g., AVO analysis and/or signal trace analysis). The analyzer component 576 can also include the spectral analysis functionality described above in reference to FIGS. 14-15.

As further shown in FIG. 17, the ultrasound system 570 can also include a component 578 that can be configured to allow correlation and/or selectivity of one or more attributes determined by the analyzer component 576. Examples of how correlations and/or selections can be performed are described below in greater detail.

Figure 18:
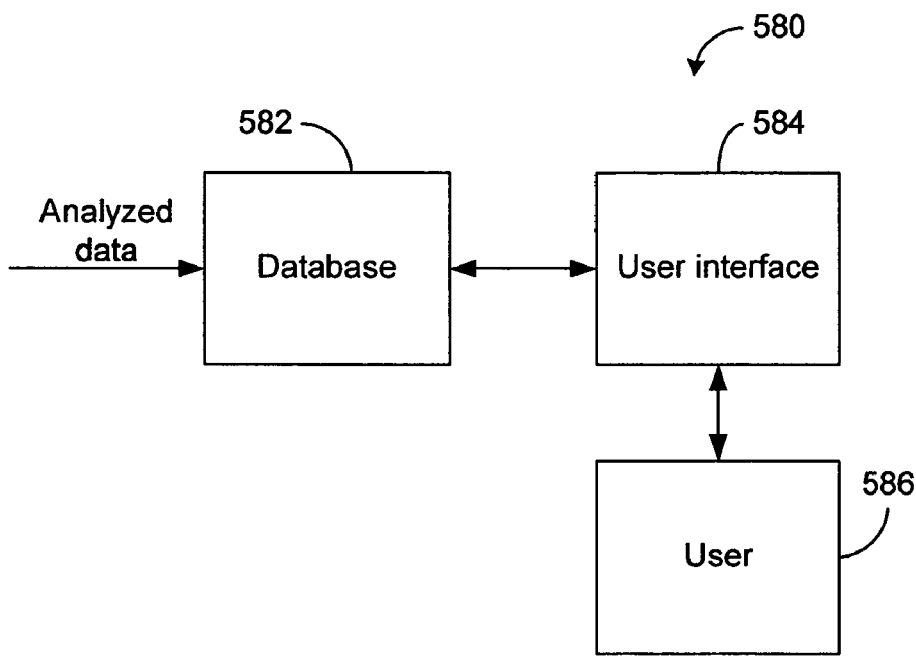
FIG. 18 shows that the determination of additional information from the presented or correlated attributes can be facilitated by a user via a user interface.

FIG. 18 shows one embodiment of an ultrasound system 580 having a database component 582 that can be configured to receive analyzed data having information about one or more attributes. The database component 582 is shown to be functionally linked to a user interface component 584 that interfaces a user 586 with the attribute data. In one embodiment, the interface component 584 can include a visual display such as a computer screen. In one embodiment, the interface component 584 can also include a user input device that allows the user 586 to select a portion of displayed data for subsequent analysis.

Figure 19A:
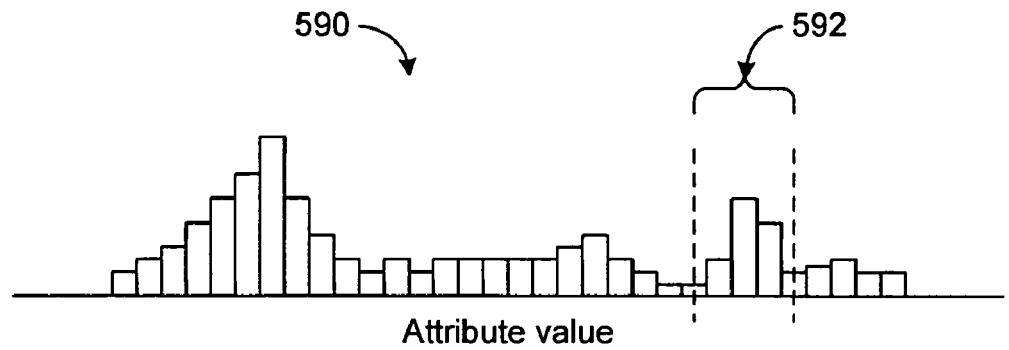
FIGS. 19A and 19B show examples of presented and correlated attributes, and portions of interest that can be identified therefrom.
Figure 19B:
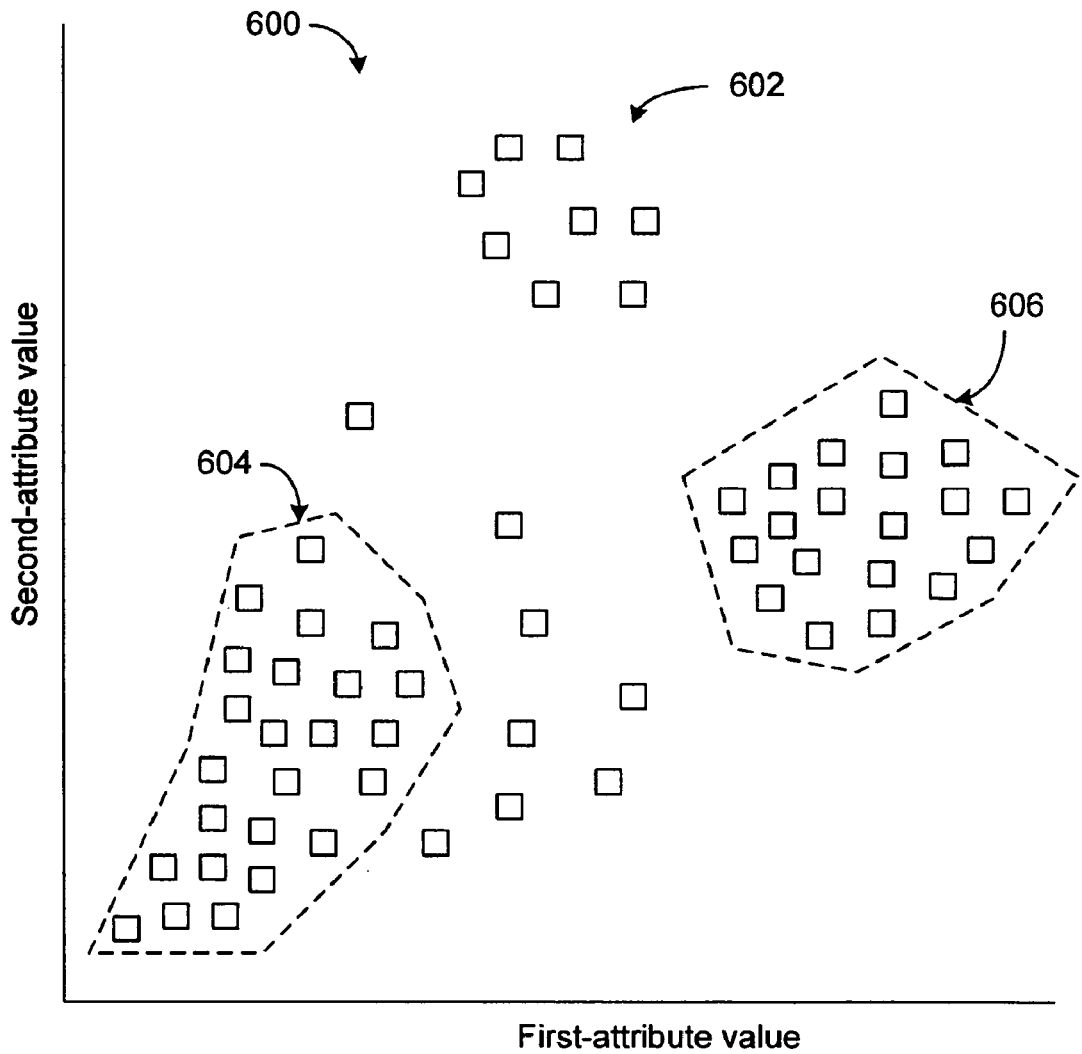

FIGS. 19A and 19B show examples of how attribute data can be presented to a user so that the user can select some portion of the data for further analysis. Such presentation of the attribute data and the selection can be facilitated by the user interface component described above in reference to FIG. 18.

FIG. 19A shows an example of a one-dimensional representation 590 of a given attribute. The given attribute can be one of the attributes obtained by the analyzer component (576 in FIG. 17), or a result of some operation on one or more attributes. The one dimensional representation 590 can be, for example, a one-dimensional histogram of values associated with the given attribute.

As further shown in FIG. 19A, the user can review the example histogram 590 and select a portion 592 for further analysis. For example, the peak structure of the selected portion 592 may indicate some anomaly in the attribute of the object being analyzed. By selecting such data and limiting the subsequent analysis to attribute(s) corresponding to those selected data, an anomalous condition may "stand out" more clearly than if presented along with the rest of the "uninteresting" data.

In one embodiment, each value of the given attribute has associated with it some form of an index. For example, the index may indicate which voxel the attribute value applies to. Thus in one embodiment, the example selection 592 of the example histogram can be thought of as selecting particular voxels within a region of interest. The selected voxels can then be analyzed further with other attributes, including imaging.

FIG. 19B shows an example of a two-dimensional representation 600 of two selected attributes. Each of the two selected attributes can be one of the attributes obtained by the analyzer component (576 in FIG. 17), or a result of some operation on one or more attributes. The two-dimensional representation 600 can be, for example, a two-dimensional display such as a scatter plot, contour plot, and the like.

The example cross-plot 600 is shown to include a plurality of data points 602, where each data point can have associated with it some form of an index. For example, the index may indicate which voxel the attribute data point applies to.

As further shown in FIG. 19B, the user can review the example cross plot 600 and select example portions such as 604 and 606. Such selections can be delineated by example "cut" lines 604 and 606. For the purpose of description, suppose that the portion 604 represents a known property of the region of interest. Then, data points within that known portion 604 can be omitted from further analysis, if so desired. Also suppose that the portion 606 represents an interesting but yet unknown property of the region of interest. The example cluster 606 may indicate some anomaly in the attribute of the object being analyzed. By selecting such data and limiting the subsequent analysis to attribute(s) corresponding to those selected data, an anomalous condition may "stand out" more clearly than if presented along with the rest of the "uninteresting" data.

Figure 20:
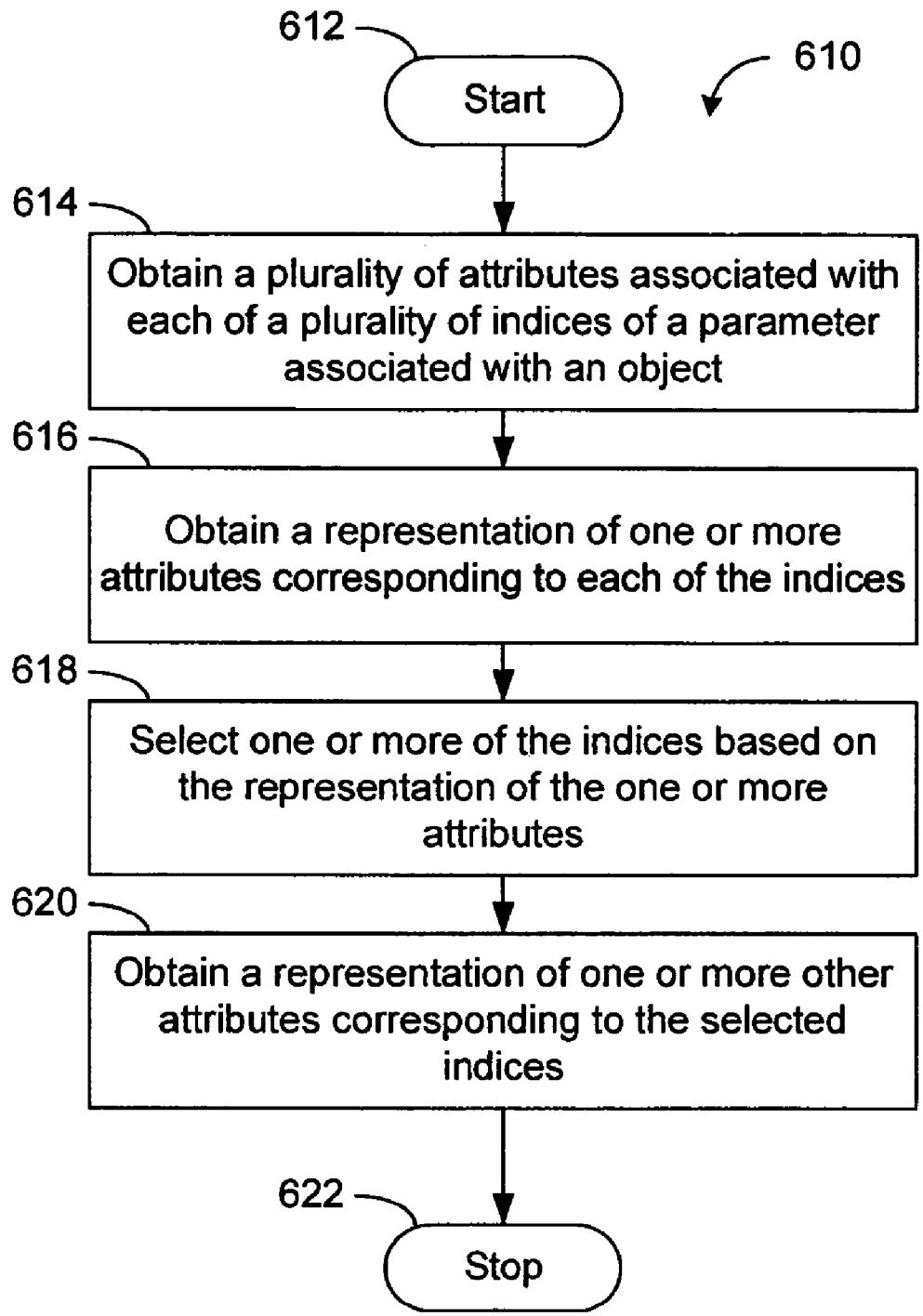
FIG. 20 shows one embodiment of a process that obtains additional information from a first set of one or more attributes and analyzes a second set of one or more attributes based on the additional information from the first set.

FIG. 20 shows one embodiment of a process 610 that can perform various forms of cross-plotting analysis as described above in reference to FIGS. 16-18. The process 610 begins in a start state 612, and in a process block 614, a plurality of attributes are obtained, where the attributes are associated with some indices associated with a region of interest. In one embodiment, the indices represent the voxels within the region of interest, and each voxel can be characterized by a plurality of attributes. In a process block 616, a representation of one or more indexed attributes is obtained. In one embodiment, the representation can be a one-dimensional histogram of a selected attribute corresponding to different indices. In another embodiment, the representation can be a two-dimensional plot of selected two attributes corresponding to different indices. In a process block 618, one or more indices (i.e., data points) are selected based on the representation of the attributes. In one embodiment, such selection can be a cut made on a portion of the one-dimensional histogram. In another embodiment, such selection can be a cut made on a portion of the two-dimensional plot. In a process block 620, a representation of one or more attributes corresponding to the selected indices is obtained, so as to allow more detailed analysis of the selected indices of interest. The process 610 ends at a stop state 622.

Figure 21A:
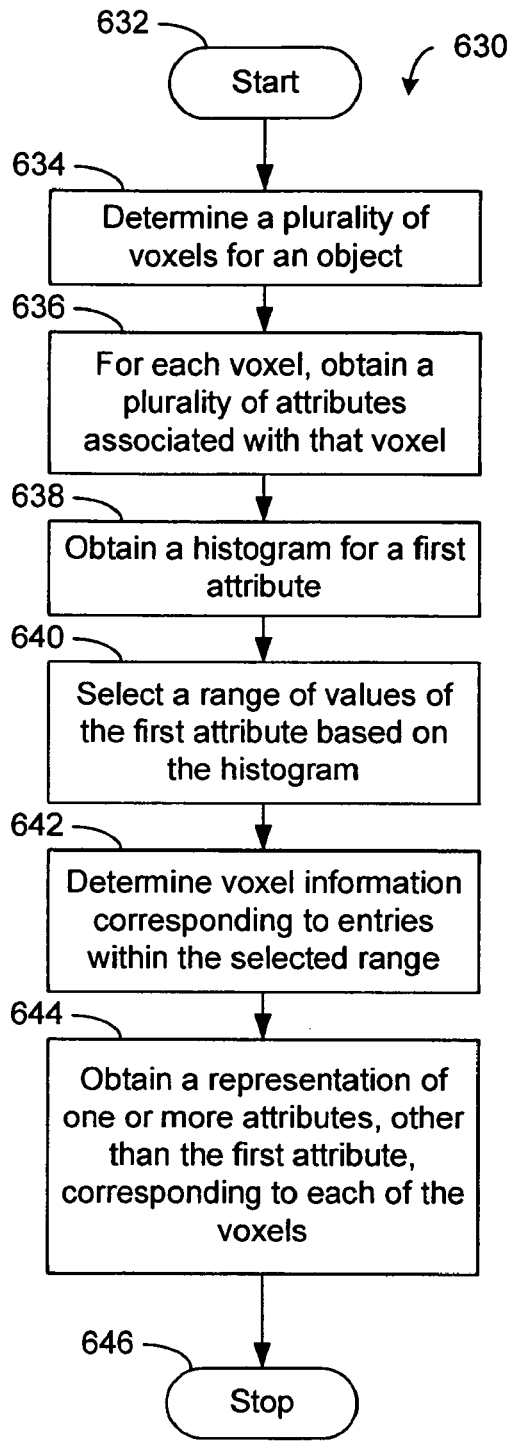
FIG. 21A shows one embodiment of a one-dimensional example of the process of FIG. 20, where information obtained from a first attribute is used so as to analyze a second attribute.
Figure 21B:
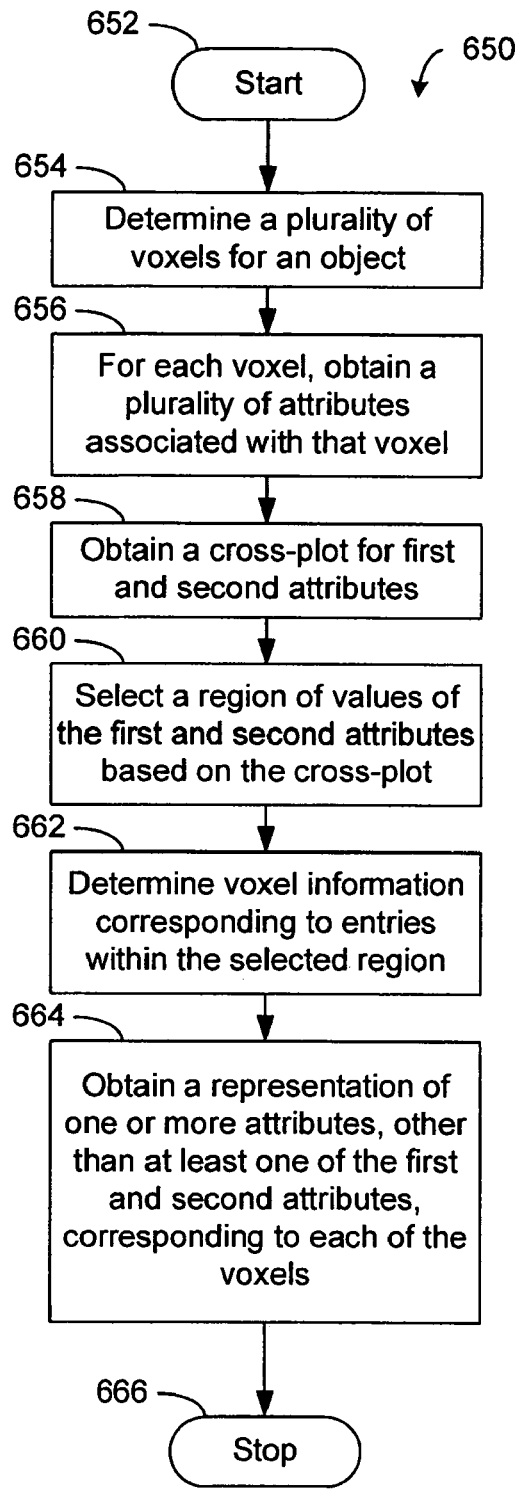
FIG. 21B shows one embodiment of a two-dimensional example of the process of FIG. 20, where information obtained from a first two-dimensional correlation is used so as to analyze a second two-dimensional correlation.

FIGS. 21A and 21B now show example processes 630, 650 that specifically relate to one- and two-dimensional plots where an index corresponds to a voxel. In one embodiment as shown in FIG. 21A, the process 630 begins at a start state 632. In a process block 634, a plurality of voxels are defined for a region of interest. In a process block 636, one or more attributes associated with each voxel are obtained. In a process block 638, a one-dimensional histogram is obtained for values corresponding to a first attribute. In a process block 640, a range of values is selected from the first attribute histogram. In a process block 642, information about voxels corresponding to the selected values are obtained. In a process block 644, a representation of one or more attributes is made for the voxels corresponding to the selected values. The representation may be another one-dimensional histogram, or a two-dimensional cross plot. In one embodiment, the new one-dimensional histogram is for a second attribute that is different than the first attribute. In one embodiment, the two attributes in the new two-dimensional cross plot includes at least one attribute that is different than the first attribute. The process 630 ends at a stop state 646.

In one embodiment as shown in FIG. 21B, the process 650 begins at a start state 652. In a process block 654, a plurality of voxels are defined for a region of interest. In a process block 656, a plurality of attributes associated with each voxel are obtained. In a process block 658, a two-dimensional cross plot is obtained for values corresponding to first and attributes. In a process block 660, a region of data points corresponding to the first and second attributes is selected from the cross plot. In a process block 662, information about voxels corresponding to the selected data points are obtained. In a process block 664, a representation of one or more attributes is made for the voxels corresponding to the selected data points. The representation may be a one-dimensional histogram, or another two-dimensional cross plot. In one embodiment, the new one-dimensional histogram can be for any attribute, including either of the first and second attributes. In one embodiment, the two attributes in the new two-dimensional cross plot includes at least one attribute that is different than the first or second attribute. The process 650 ends at a stop state 666.

Figure 22:
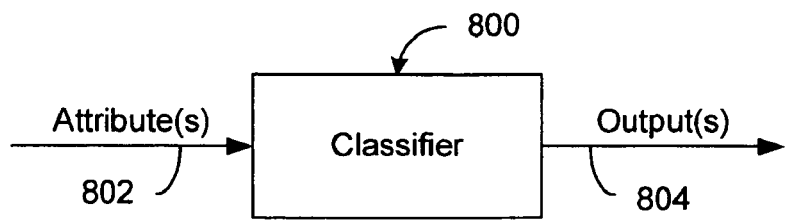
FIG. 22 shows one embodiment of a classifier that determines one or more result outputs based on input of one or more attributes.

FIG. 22 shows one example way of using the various attributes obtained as described herein. In one embodiment, a classifier 800 can be configured to receive one or more attributes (depicted as an arrow 802) and determine one or more results based on the input attribute(s). Such results can then be output, as depicted by an arrow 804. Such result-determination based on attribute-input(s) can be used in a number of ways. For example, one or more attributes corresponding to a volume of a tissue can be obtained. Such attributes can be fed into the classifier that determines whether the tissue in question can be classified as, for example, normal or abnormal. In another example, attributes corresponding to a material being inspected can be fed into the classifier. The classifier can then determine whether the material passes the inspection or not based on the input attributes.

Figure 23A:
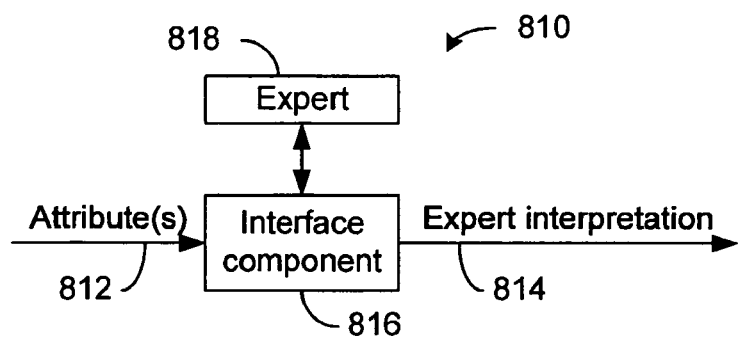
FIGS. 23A to 23C show some example embodiments of the classifier of FIG. 22.
Figure 23B:
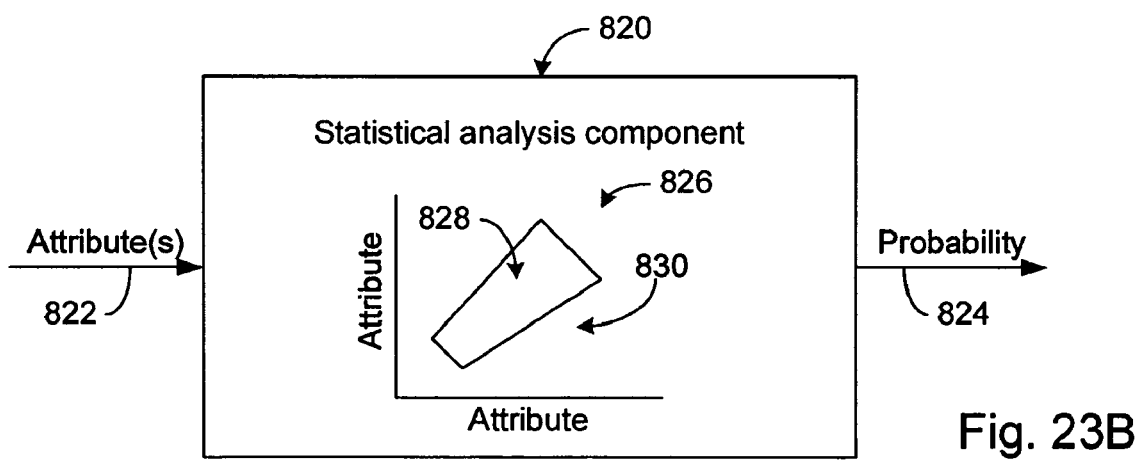
Figure 23C:
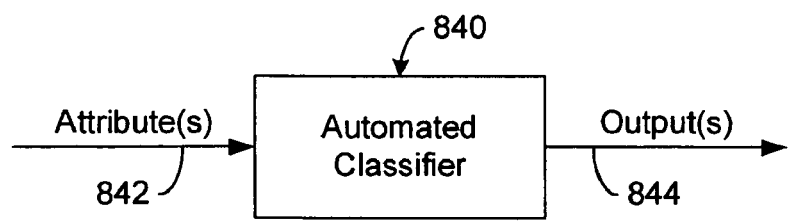

FIGS. 23A to 23C show by examples some possible embodiments of the classifier 800 described above in reference to FIG. 22. FIG. 23A shows one embodiment of a classifier component 810 that receives one or more attributes 812 and outputs an expert interpretation 814. Such interpretation can be facilitated by an interface component 816 that is configured to interface the input attributes to an expert 818. In one example, the interface component 816 can include a display device that is configured to display a visual representation (e.g., one or more cross-plots of attributes) of the attributes corresponding to a volume of the medium in question. Based on the visual representation, the expert can determine whether the volume in question is within or outside of some norm.

FIG. 23B shows another embodiment of a classifier component that includes a statistical analysis component 820. The statistical analysis component 820 can be configured to perform statistical analysis on an input of one or more attributes 822 and output a result such as a probability value 824. Such probability value can indicate, for example, a likelihood of the input attributes being classified in a given class. For example, suppose that a "cross-plot" 826 (for the purpose of statistical analysis, such cross-plot does not necessarily need to be presented visually) of two attributes defines an example normal range 828 and an abnormal range 830. If the input attributes maps to the abnormal range 830, statistical analysis can be performed to estimate what the likelihood of abnormal condition may be.

FIG. 23C shows another embodiment of a classifier component 840 that can be configured to operate substantially automatically, so that given one or more attributes as inputs 842, the automated classifier 840 can determine and output one or more results 844. Such automation of classifying can be achieved in a number of ways, including, for example, by neural network type processes configured for functionalities such as pattern recognition.

In one embodiment, a classifier component can include some or all of the example functionalities described above in reference to FIGS. 23A to 23C. For example, a classifier can be configured to generally operate automatically once "trained" and calibrated. The automated functionality can include, for example, determination of normal/abnormal and/or the probabilistic estimate thereof.

Figure 24:
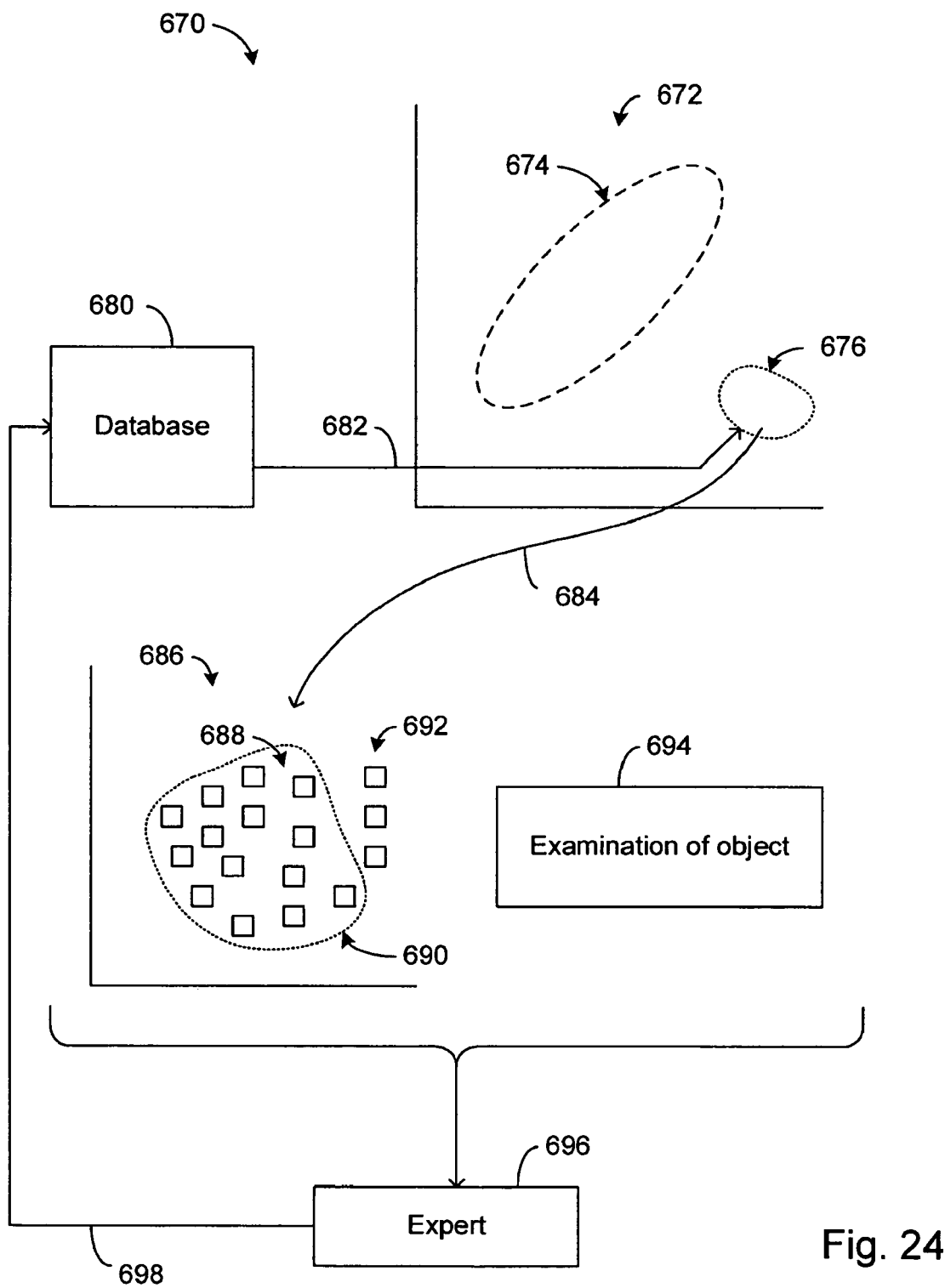
FIG. 24 shows an example of how some of the classifiers can be programmed, calibrated, and/or refined for either automated or supervised modes of operation.

FIG. 24 now shows an example application 670 that can be used to train and calibrate the various embodiments of the classifier described above in reference to FIGS. 22 and 23. The example application 670 can also be used as an expert-based supervised classifier.

In one embodiment, the attribute determination and cross plotting techniques as described herein can be utilized to obtain a better understanding of various characteristics of a region of interest. Information gained therefrom can then be used to train the classifier what to look for and where to look. Such information can also be used to successively "fine-tune" the existing base of knowledge, so that subsequent classifying operations (automated or supervised) can be made more accurate.

As describe above by examples, some attributes do not necessarily correspond directly to physical or mechanical properties. Also, some attributes may be estimated by use of assumptions that may or may not be completely accurate (e.g., reflectivity values $R_P$ and $R_S$ being estimated by using an assumption that compressional velocity is approximately twice that of the shear velocity).

In some embodiments of the present teachings, however, the obtained attributes do not necessarily need to be substantially the same as some standard values. For example, values obtained for mechanical parameters such as rigidity parameter $\mu$ and bulk modulus $\kappa$ do not necessarily need to conform to some standard values for known materials (such as animal tissues). In various applications, it is the relative values of the attributes that can be useful. So in the foregoing example of the mechanical properties, even if the values for $\mu$ and $\kappa$ are generally different from the standard values, self-consistent differences of the values within the region of interest can provide useful information. For example, anomalous values of mechanical attributes in a portion of the region of interest may indicate some anomaly for that portion. Being able to determine such anomaly using different attributes can improve the manner in which tissue can be characterized.

The foregoing tissue characterization can be further enhanced by introduction of an expert that can empirically observe the anomaly guided by the attributes. The empirical observation can be used to update and improve the meaning of the obtained attributes. Such increase in the body of useful knowledge can then be beneficial for classifier training/calibration purpose, and also for subsequent characterization of regions of interest, such as animal tissues.

Thus as shown in FIG. 24, the example application 670 is shown to include an example cross plot 672 displaying a first set of attributes. In one embodiment, such attributes are obtained from a database 680. Within the cross plot 672, an example known pattern is indicated as a region 674, and a pattern representing an anomaly is indicated as a region 676. The anomalous region 676 is shown to be analyzed further, as indicated by a curved arrow 684, via a second cross plot 686 where a second set of attributes are displayed based on the voxel indices of the selected anomalous region 676. The second set of attributes may or may not be the same as the first set.

As further shown in FIG. 24, an expert 696 is shown to be analyzing the second cross plot 686 (where the anomaly based on the first plot 672 is displayed as data points 688) and an examination of the region of interest (which can be direct or otherwise). The expert 696 is shown to "update" the "definition" of the anomalous region in the second plot 686, based on information obtained from the examination 694. The updated anomalous region 690 is shown to now exclude data points 692 and the updated anomalous region information is returned to the database, indicated by arrow 698.

As further shown in FIG. 24, the updated characterization of the anomaly in the foregoing manner is shown to update the database 680. Such updated database can be used to characterize other anomalies more accurately in subsequent analyses. Such updated database can also be used to refine various operating parameters used by various embodiments of classifiers. For example, the boundaries that define normal and abnormal tissue characteristics can be refined so that subsequent normal/abnormal determination can be made more accurately.

Figure 25:
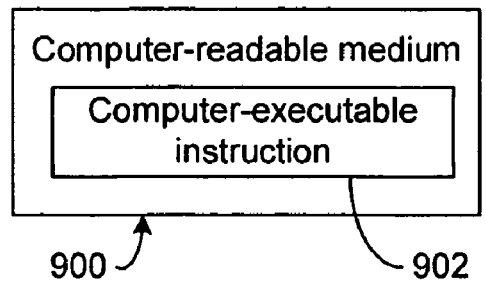
FIG. 25 shows one embodiment of a computer-readable medium having a computer-executable instruction that can be configured to process a signal and generate one or more attributes.

FIG. 25 shows one embodiment of a computer-readable medium 900 having a computer-executable instruction 902 that can be configured to process a signal and generate one or more attributes. In one embodiment, the signal is based on an acoustic energy that has been reflected from a medium. In one embodiment, the one or more attributes are attributes associated with an animal tissue. As described herein, attributes of the animal tissue could be used for medical or non-medical purposes. In one embodiment, the one or more attributes are associated with mediums associated with non-seismic materials.

Figure 26:
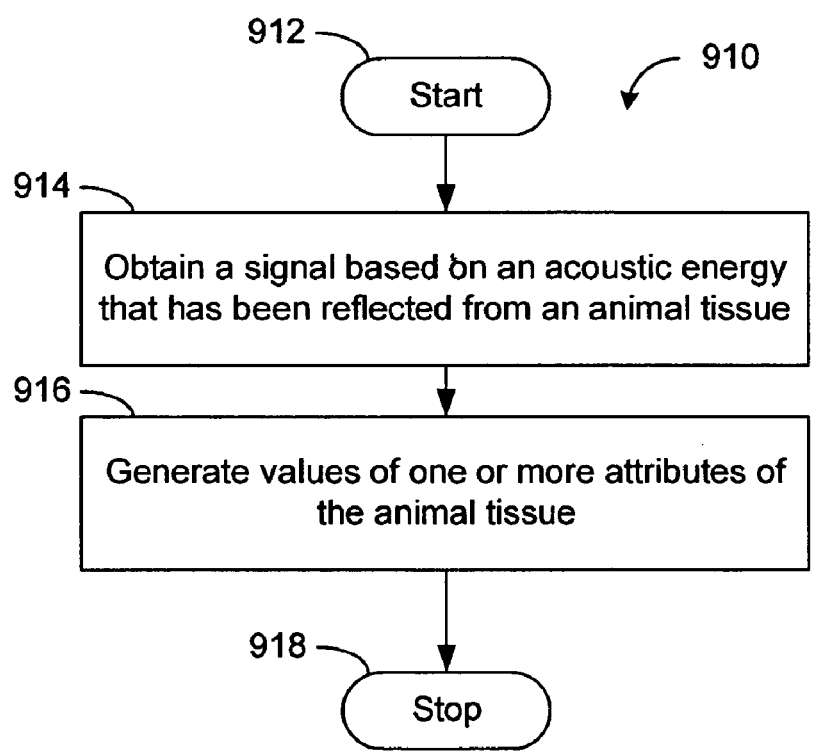
FIG. 26 shows one embodiment of the computer-executable instruction of FIG. 25.

FIG. 26 shows one example of a process 910 that can implement the computer-executable instruction 902 of FIG. 25. The process 910 begins at a start state 912. In a process block 914, the process 910 obtains a signal based on an acoustic energy that has been reflected from a medium. The medium can be an animal tissue or other non-seismic materials. In a process block 916, the process 910 generates one or more values of one or more attributes associated with the medium. In one embodiment, the process 910 generates values associated with at least two attributes. The process 910 ends at stop state 918.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

What is claimed is:

1. Apparatus for determining one or more attributes of an animal tissue using acoustic energy, the apparatus comprising:
   an acoustic receiver module that receives acoustic energy that has been reflected from the animal tissue, and outputs an electrical signal based on the received acoustic energy;
   a display component;
   a user interface;
   a processor that is configured to process the signal to generate one or more sets of values of each of the one or more attributes of said animal tissue, said processor configured to:
   determine one or more characteristics of the acoustic energy, the one or more characteristics selected from the group consisting of:
   an amplitude-variations-with-offset characteristic,
   a signal trace characteristic,
   a spatial characteristic, and
   a spectral decomposition characteristic;
   generate the sets of the attribute values based on the one or more characteristics;
   associate each of the attribute values with one or more voxels in a region of interest in said animal tissue;
   display on the display component a representation of data points corresponding to at least one of the sets of attribute values the data points displayed at locations determined by the corresponding attribute values;
   receive by way of the user interface input selecting a subset of the data points; and
   perform subsequent analysis on a subset of the voxels corresponding to attribute values corresponding to the subset of the data points; and
   a computer storage configured to store the values of the one or more attributes of the animal tissue.

2. The apparatus of claim 1, wherein the processor is configured to obtain the values for at least two of the attributes from said amplitude-variations-with-offset characteristic.

3. The apparatus of claim 1, wherein the processor is configured to obtain the values for at least two of the attributes from said signal trace characteristic.

4. The apparatus of claim 1, wherein the processor is configured to obtain the values for at least two of the attributes from said spectral decomposition characteristic.

5. The apparatus of claim 1, wherein the processor is configured to determine the values for at least one of the attributes from said
   amplitude-variations-with-offset characteristic, and the values for at least another one of the attributes from said signal trace characteristic.

6. The apparatus of claim 1, wherein the processor is configured to determine the values for at least one of the attributes from said
   amplitude-variations-with-offset characteristic, and to determine values for at least another one of the attributes from said spectral decomposition characteristic.

7. The apparatus of claim 1, wherein the processor is configured to determine the values for at least one of the attributes from said signal trace characteristic, and to determine the values for at least another one of the attributes from said spectral decomposition characteristic.

8. The apparatus of claim 1, wherein the processor is configured to determine the values for at least one of the attributes from a spatial characteristic of the acoustic energy.

9. The apparatus of claim 8, wherein the processor is configured to determine the values for at least one of the attributes from said
   amplitude-variations-with-offset characteristic, and to determine the values for at least another one of the attributes from said spatial characteristic.

10. The apparatus of claim 8, wherein the processor is configured to determine the values for at least one of the attributes from said signal trace characteristic, and to determine the values for at least another one of the attributes from said spatial characteristic.

11. The apparatus of claim 8, wherein the processor is configured to determine the values for at least one of the attributes from said spatial characteristic, and to determine the values for at least another one of the attributes from said spectral decomposition characteristic.

12. The apparatus of claim 1 wherein the data points correspond to corresponding pairs of the values for a first pair of the attributes.

13. The apparatus of claim 12 wherein the display component is configured to display an additional representation of data points corresponding to corresponding pairs of the values for a second pair of said attributes, said values for the second pair of attributes corresponding to said voxels of the selected subset of the data points.

14. The apparatus of claim 12 wherein the display component is configured to display an additional representation of data points corresponding to corresponding pairs of the values for a second pair of said attributes, said values for the second pair of attributes corresponding to said voxels of the selected subset of the data points.

15. The apparatus of claim 1, wherein the processor is configured to set the values for one of the attributes to values of the amplitude-variations-with-offset characteristic.

16. The apparatus of claim 15, wherein the acoustic energy includes acoustic energy that has been reflected in the animal tissue through a plurality of angles θ and the amplitude-variations-with-offset characteristic comprises a relationship between a plurality of values derived from said received acoustic energy and the corresponding reflection angles θ, said reflection angles θ being with respect to a location on a layer in the animal tissue.

17. The apparatus of claim 16, wherein the plurality of values comprise reflection amplitudes and the processor is configured to estimate a functional relationship R from the plurality of values and the corresponding reflection angles.

18. The device of claim 17, wherein the functional relationship R comprises a relationship $R(\theta)=A+B \sin^2\theta+C \sin^2\theta \tan^2\theta$ where parameters A, B, and C are constants.

19. The device of claim 18, wherein said processor is further configured so as to estimate values $R_{P0}$ and $R_{S0}$ respectively corresponding to zero-offset reflectivity of a compressional component of said received acoustic energy and zero-offset reflectivity of a shear component of said received acoustic energy.

20. The apparatus of claim 19, wherein said processor is configured to estimate the values $R_{P0}$ and $R_{S0}$ respectively by the approximations $R_{P0}=A$ and $R_{S0}=(4A-9B+5C)/8$.

21. The apparatus of claim 16, wherein the processor is configured to estimate from the plurality of values and the corresponding reflection angles one or more parameters defining a functional relationship between the values and $\sin^2\theta$.

22. The device of claim 21, wherein the functional relationship $R(\theta)$ comprises a relationship $R(\theta)=A+B \sin 2\theta$, where A and B are parameters.

23. The apparatus of claim 22, wherein the processor is further configured to estimate values $R_{P0}$ and $R_{S0}$ respectively corresponding to zero-offset reflectivity of a compressional component of said received acoustic energy and zero-offset reflectivity of a shear component of said received acoustic energy.

24. The apparatus of claim 23, wherein the processor is configured to estimate the values $R_{P0}$ and $R_{S0}$ respectively as $R_{P0}=A$ and $R_{S0}=(A-B)/2$.

25. The apparatus of claim 23, wherein the processor is further configured to invert $R_{P0}$ and $R_{S0}$ to obtain estimated values of impedance $Z_P$ and $Z_S$ respectively corresponding to compressional and shear components of said animal tissue.

26. The apparatus of claim 25, wherein the processor is further configured to estimate one or more elastic properties of said animal tissue based on said estimated impedance values $Z_P$ and $Z_S$.

27. The apparatus of claim 26, wherein said one or more elastic properties comprise a rigidity parameter $\mu$ estimated by a relationship $\mu=Z_S^2/\rho$, where $\rho$ represents an estimate of the density of said animal tissue.

28. The apparatus of claim 27, wherein said one or more elastic properties further comprise an elastic parameter $\lambda$, said elastic parameter $\lambda$ estimated by a relationship $\lambda=(Z_P^2-2Z_S^2)/\rho$.

29. The apparatus of claim 28, wherein said one or more elastic properties further comprise a parameter $\kappa$ estimated by a relationship $\kappa=\lambda+(2/3)\mu$.

30. The apparatus of claim 1, wherein the processor is configured to set the values for one of the attributes to values of the signal trace characteristic.

31. The apparatus of claim 30, wherein the signal trace characteristic comprises a complex function $F(t)=f(t)+ig(t)$, where $f(t)$ constitutes a real part of $F(t)$ and $g(t)$ constitutes an imaginary part of $F(t)$ and said processor is configured to determine $g(t)$ by computing a Hilbert transform of $f(t)$.

32. The apparatus of claim 31, wherein the signal trace characteristic further comprises a modulus $E(t)$ of said complex function $F(t)$ expressed as $E(t)=(f^2(t)+g^2(t))^{1/2}$.

33. The apparatus of claim 32, wherein the signal trace characteristic comprises a rate of change of said $E(t)$ with respect to time.

34. The apparatus of claim 32, wherein the signal trace characteristic comprises a second derivative of said $E(t)$ with respect to time.

35. The apparatus of claim 30, wherein said signal trace characteristic comprises a function representing an envelope of said electrical signal.

36. The apparatus of claim 31, wherein the signal trace characteristic comprises a substantially instantaneous phase of said received acoustic energy associated with said given region in said animal tissue, said phase being expressed as $\Phi(t)=\arctan(g(t)/f(t))$.

37. The apparatus of claim 36, wherein said phase $\Phi(t)$ is substantially independent from an amplitude of $F(t)$.

38. The apparatus of claim 36, wherein the signal trace characteristic comprises a substantially instantaneous frequency of said received acoustic energy associated with said given region in said animal tissue, said frequency being expressed as $\omega(t)=d(\Phi(t))/dt$.

39. The apparatus of claim 38, wherein the signal trace characteristic comprises a substantially instantaneous acceleration of said received acoustic energy associated with said given region in said animal tissue, said acceleration being expressed as $a(t)=d\omega(t)/dt$.

40. The apparatus of claim 38, wherein the signal trace characteristic comprises a mean frequency $\omega_{mean}(t)$ of said received acoustic energy associated with said given region in said animal tissue, said signal trace characteristic being obtained by a method performed by said processor, the method comprising:

determining a Fourier transform $F(\omega)$ of said function $F(t)$;

determining an autocorrelation function $P(\omega)$ by a relationship $P(\omega)=F(\omega)F^*(\omega)$, where $F^*(\omega)$ comprises a complex conjugate of $F(\omega)$;

determining a normalized autocorrelation function $A(t)$ by a relationship $$A(t) = \int_{\omega=0}^{\infty} P(\omega)\exp(i\omega t)d\omega \bigg/ \int_{\omega=0}^{\infty} P(\omega)d\omega;$$

and determining said mean frequency $\omega_{mean}$ by a relationship $$\omega_{mean}(t) = dA(t)/dt = -i\int_{\omega=0}^{\infty} \omega P(\omega)\exp(i\omega t)d\omega \bigg/ \int_{\omega=0}^{\infty} P(\omega)d\omega.$$

41. The apparatus of claim 40, wherein the signal trace characteristic comprises a thin-layer indicator parameter determined by a relationship $\omega(t)-\omega_{mean}(t)$.

42. The apparatus of claim 40, wherein the signal trace characteristic comprises an acceleration of said received acoustic energy associated with said given region in said animal tissue, said acceleration determined by a relationship $|d^2A(t)/dt^2|$.

43. The apparatus of claim 40, wherein the signal trace characteristic comprises a centroid frequency $\omega_c$ of a power spectrum given by a relationship $$\omega_c = \int_{\omega=0}^{\infty} \omega P(\omega)d\omega \bigg/ \int_{\omega=0}^{\infty} P(\omega)d\omega.$$

44. The apparatus of claim 40, wherein the signal trace characteristic comprises a variance $\omega_v$ to said centroid frequency $\omega_c$ given by a relationship $$\omega_v = \int_{\omega=0}^{\infty} (\omega - \omega_c)^2 P(\omega) d\omega \Big/ \int_{\omega=0}^{\infty} P(\omega) d\omega.$$

45. The apparatus of claim 40, wherein the signal trace characteristic comprises a root-mean-square frequency $\omega_{RMS}$ given by a relationship $$\omega_{RMS} = sqrt\left[\int_{\omega=0}^{\infty} \omega^2 P(\omega) d\omega \Big/ \int_{\omega=0}^{\infty} P(\omega) d\omega\right].$$

46. The apparatus of claim 1, wherein the processor is configured to set the values for one of the attributes to values of the spatial characteristic.

47. The apparatus of claim 46, wherein the spatial characteristic comprises information about a propagation number k associated with the received acoustic energy.

48. The apparatus of claim 47, wherein the spatial characteristic comprises a longitudinal component $k_z=(\omega/v)\cos\theta$ and a transverse component $k_r=(\omega/v)\sin\theta$ of the propagation number k, where $\theta$ represents an arrival angle associated with the received acoustic energy.

49. The apparatus of claim 48, wherein the spatial characteristic comprises a time gradient dt/dx along a selected transverse direction x.

50. The apparatus of claim 49, wherein the time gradient dt/dx is proportional to $\sin\theta/v$.

51. The apparatus of claim 49, wherein the time gradient dt/dx is proportional to $kx/\omega$, where $\omega$ represents the frequency associated with the received acoustic energy.

52. The apparatus of claim 51, wherein the frequency $\omega$ is estimated by a centroid frequency $\omega_c$ associated with the received acoustic energy.

53. The device of claim 51, wherein the frequency $\omega$ is estimated by an autocorrelation function A(t) associated with the received acoustic energy, evaluated at one time lag, so that $\omega=\arg|A(1)|$.

54. The apparatus of claim 49, wherein the spatial characteristic comprises a time gradient dt/dy along a selected transverse direction y that is substantially perpendicular to the direction x.

55. The apparatus of claim 54, wherein the spatial characteristic comprises an azimuthal time gradient expressed as $$\Delta\Phi = \arctan\left(\frac{\frac{dt}{dy}}{\frac{dt}{dx}}\right).$$

56. The apparatus of claim 54, wherein the spatial characteristic comprises a transverse time gradient expressed as $\Delta T=sqrt[(dt/dx)^2+(dt/dy)^2]$.

57. The apparatus of claim 56, wherein the spatial characteristic comprises a lateral continuity estimated as $\Delta^2 T=sqrt[(d^2t/dx^2)^2+(d^2t/dy^2)^2]$.

58. The apparatus of claim 1, wherein the processor is configured to set the values for one of the attributes to values of the spectral decomposition characteristic.

59. The apparatus of claim 58, wherein said spectral decomposition analysis comprises performing said processing of the electrical signal at one or more ranges of frequency associated with said electrical signal.

60. The apparatus of claim 1, wherein the display component is configured to display simultaneously the values of at least two of the attributes for a plurality of voxels contained in a region of interest of the animal tissue.

61. The apparatus of claim 1, wherein said processor is configured to classify said voxels based on said associated attribute values.

62. The apparatus of claim 61, wherein said processor is configured to generate a result value based on the classifying of the voxels.

63. The apparatus of claim 62, wherein the classifying of the voxels and the generating of the result are performed substantially automatically.

64. Apparatus according to claim 1 wherein the representation comprises a plurality of dimensions.

65. Apparatus according to claim 1 wherein the representation comprises a histogram.

66. Apparatus according to claim 1 wherein the representation comprises a scatter plot.

67. Apparatus according to claim 1 wherein the representation comprises a contour plot.

68. Apparatus according to claim 1 wherein the representation comprises a cross plot.

69. Apparatus according to claim 1 wherein the representation comprises a two-dimensional representation and the data points correspond to ordered pairs of values for first and second attributes corresponding to the same voxel.

70. Apparatus according to claim 1 wherein the processor, when performing the subsequent analysis, is configured to display on the display component a second representation of data points corresponding to ne or more attributes of the voxels corresponding to the selected subset.

71. Apparatus according to claim 70 wherein the second representation is based on at least one set of attribute values not included in the first representation.

72. A method, for determining attributes of an animal tissue using acoustic energy, the method comprising:
receiving acoustic energy that has been reflected from the animal tissue;
generating an electrical signal from the received acoustic energy;
processing the electrical signal to determine one or more characteristics of the acoustic energy, the one or more characteristics selected from the group consisting of:
an amplitude-variations-with-offset characteristic,
a signal trace characteristic,
a spatial characteristic, and
a spectral decomposition characteristic;
generating one or more sets of values for one or more attributes of said animal tissue based on the one or more characteristics;
associating each attribute value with one or more voxels in a region of interest in said animal tissue;
displaying a representation of data points corresponding to at least one of the sets of attribute values the data points displayed at locations determined by the corresponding attribute values;
receiving user input selecting a subset of the data points;
performing subsequent analysis on a subset of the voxels corresponding to attribute values corresponding to the selected subset of the data points; and
storing the values of the one or more attributes in a computer storage.

73. Apparatus for determining one or more attributes of tissue using acoustic energy, the apparatus comprising:

an acoustic receiver operative to receive acoustic energy that has been reflected from the tissue, and to output an electrical signal based on the received acoustic energy;
a display;
a user interface;
a processor configured to:
  process the signal to determine values for the one or more attributes for each of a plurality of voxels in a region of interest in said tissue;
  display on the display indicia corresponding to the voxels, the indicia displayed at locations that, for at least one dimension, correspond to values of one of the attributes that is associated with the dimension;
  select a subset of the voxels based on the corresponding values for the attribute; and
  perform further analysis on the selected subset of the voxels.

74. Apparatus according to claim 73 wherein the processor, when performing further analysis on the selected subset of the voxels, is configured to display on the display an image of the selected subset of the voxels.

75. Apparatus according to claim 73 wherein the processor, when displaying on the display indicia corresponding to the voxels, is configured to display a two-dimensional representation wherein the indicia are displayed at locations that, for a first dimension, correspond to values of a first one of the attributes that is associated with the first dimension and for a second dimension, correspond to values of a second one of the attributes that is associated with the second dimension.

76. Apparatus according to claim 75 wherein the two-dimensional representation comprises a scatter plot.

77. A method for determining attributes of an animal tissue using acoustic energy, the method comprising:
  receiving acoustic energy that has been reflected from the animal tissue;
  generating an electrical signal from the received acoustic energy;
  processing the signal to determine values for one or more attributes for each of a plurality of voxels in a region of interest in said animal tissue;
  displaying on the display indicia corresponding to the voxels, the indicia displayed at locations that, for at least one dimension, correspond to values of one of the attributes that is associated with the dimension;
  selecting a subset of the voxels based on the corresponding values for the attribute; and
  performing further analysis on the selected subset of the voxels.

78. A method according to claim 77 wherein performing further analysis on the selected subset of the voxels comprises displaying on the display an image of the selected subset of the voxels.

79. A method according to claim 77 wherein displaying on the display indicia corresponding to the voxels comprises displaying a two-dimensional representation wherein the indicia are displayed at locations that, for a first dimension, correspond to values of a first one of the attributes that is associated with the first dimension and for a second dimension, correspond to values of a second one of the attributes that is associated with the second dimension.

80. A method according to claim 79 wherein the two-dimensional representation comprises a scatter plot.

* * * * *